US009428768B2

(12) United States Patent
Pham et al.

(10) Patent No.: US 9,428,768 B2
(45) Date of Patent: *Aug. 30, 2016

(54) METHOD FOR THE PRODUCTION AND PURIFICATION OF ADENOVIRAL VECTORS

(75) Inventors: Hai Pham, Houston, TX (US); Shuyuan Zhang, Sugar Land, TX (US); Peter Clarke, Sugar Land, TX (US)

(73) Assignee: Crucell Holland B.V., Leiden (NL)

( * ) Notice: Subject to any disclaimer, the term of this patent is extended or adjusted under 35 U.S.C. 154(b) by 1799 days.

This patent is subject to a terminal disclaimer.

(21) Appl. No.: 12/607,791

(22) Filed: Oct. 28, 2009

(65) Prior Publication Data

US 2010/0105124 A1    Apr. 29, 2010

Related U.S. Application Data

(63) Continuation of application No. 11/187,319, filed on Jul. 22, 2005, now abandoned, which is a continuation-in-part of application No. 09/203,078, filed on Dec. 1, 1998, now Pat. No. 7,732,129.

(60) Provisional application No. 60/624,627, filed on Nov. 3, 2004.

(51) Int. Cl.
| C12N 7/02 | (2006.01) |
| C12N 15/86 | (2006.01) |
| C12N 7/00 | (2006.01) |
| C12N 15/10 | (2006.01) |
| C12Q 1/70 | (2006.01) |
| A61K 48/00 | (2006.01) |

(52) U.S. Cl.
CPC ............ *C12N 15/86* (2013.01); *C12N 7/00* (2013.01); *C12N 15/1017* (2013.01); *C12Q 1/70* (2013.01); *A61K 48/00* (2013.01); *C12N 2710/10343* (2013.01); *C12N 2710/10351* (2013.01)

(58) Field of Classification Search
None
See application file for complete search history.

(56) References Cited

U.S. PATENT DOCUMENTS

| 4,352,883 A | 10/1982 | Lim ........................ 435/178 |
| 4,725,547 A | 2/1988 | Sakamoto et al. ............ 435/239 |
| 4,797,368 A | 1/1989 | Carter et al. .................. 435/320 |
| 5,106,841 A | 4/1992 | Scheer ........................ 514/185 |
| 5,139,941 A | 8/1992 | Muzyczka et al. ......... 435/172.3 |
| 5,552,309 A | 9/1996 | March ........................ 435/172.3 |
| 5,607,851 A | 3/1997 | Pellegrini et al. ............. 435/236 |
| 5,648,251 A * | 7/1997 | Kotani et al. ................ 435/456 |
| 5,670,488 A | 9/1997 | Gregory et al. ............. 514/44 R |
| 5,733,720 A | 3/1998 | Olivo ........................... 435/5 |
| 5,744,304 A | 4/1998 | Munford ..................... 435/6 |
| 5,789,244 A | 8/1998 | Heidrum et al. ............. 435/320.1 |
| 5,824,544 A | 10/1998 | Armentano et al. ....... 435/320.1 |
| 5,837,520 A | 11/1998 | Shabram et al. ............. 435/239 |
| 5,932,210 A | 8/1999 | Gregory ..................... 424/93.2 |
| 5,965,358 A | 10/1999 | Carrion et al. ................ 435/5 |
| 6,143,548 A | 11/2000 | O'Riordan et al. ......... 435/239 |
| 6,194,191 B1 | 2/2001 | Zhang et al. ................ 435/239 |
| 6,194,210 B1 | 2/2001 | Leu et al. .................... 435/403 |
| 6,261,823 B1 | 7/2001 | Tang et al. .................. 435/239 |
| 6,316,185 B1 | 11/2001 | Saifer et al. ................... 435/5 |
| 6,383,795 B1 | 5/2002 | Carrion et al. ............... 435/229 |
| 6,447,995 B1 | 9/2002 | Carrion et al. ................ 435/5 |
| 6,485,958 B2 | 11/2002 | Blanche et al. ............. 435/239 |
| 6,537,793 B2 | 3/2003 | Blanche et al. ............. 435/239 |
| 6,586,226 B2 | 7/2003 | Carrion et al. ............. 435/239 |
| 6,630,299 B2 | 10/2003 | Carrion et al. ................ 435/5 |
| 6,689,600 B1 | 2/2004 | Wu et al. .................... 435/235.1 |
| 6,726,904 B2 | 4/2004 | Krauss et al. ............... 424/78.17 |
| 6,905,862 B2 | 6/2005 | Blanche et al. ............. 435/239 |
| 7,125,706 B2 | 10/2006 | Zhang et al. ................ 435/235.1 |
| 2006/0275781 A1 | 12/2006 | Pham et al. ................... 435/329 |

FOREIGN PATENT DOCUMENTS

| EP | 0273085 | 12/1986 |
| EP | 0475623 | 3/1992 |
| JP | 1279843 | 11/1989 |
| JP | 04-009338 | 1/1992 |
| WO | WO 93/18790 | 9/1993 |
| WO | WO 93/25224 | 12/1993 |
| WO | WO 94/06910 | 3/1994 |
| WO | WO 94/17178 | 8/1994 |
| WO | WO 95/06743 | 3/1995 |
| WO | WO 95/10601 | 4/1995 |
| WO | WO 95/19427 | 7/1995 |
| WO | WO 95/24468 | 9/1995 |
| WO | WO 95/25789 | 9/1995 |
| WO | WO 96/09399 | 3/1996 |
| WO | WO 96/27677 | 9/1996 |
| WO | WO 96/32116 | 10/1996 |
| WO | WO 97/04803 | 2/1997 |
| WO | WO 97/08298 | 3/1997 |
| WO | WO 98/00524 | 1/1998 |
| WO | WO 98/22588 | 5/1998 |

(Continued)

OTHER PUBLICATIONS

U.S. Appl. No. 60/203,078.
Aboud et al., "Rapid purification of extracellular and intracellular Moloney murine leukemia virus," *Arch. Viol*., 71:185-195, 1982.
Arap et al., "Replacement of the *p16/CDKN2* gene suppresses human glioma cell growth," *Cancer Res.*, 55:1351-1354, 1995.
Baichwal and Sugden, "Vectors for gene transfer derived from animal DNA viruses: Transient and stable expression of transferred genes," In: Kucherlapati R, ed. Gene transfer. New York: Plenum Press, pp. 117-148, 1986.
Batra et al., "IkappaBalpha gene transfer is cytotoxic to squamous-cell lung cancer cells and sensitizes them to tumor necrosis factor-alpha-mediated cell death," *Am. J. Respir. Cell Mol. Biol.*, 21(2):238-45, 1999.

(Continued)

*Primary Examiner* — Michael Burkhart
(74) *Attorney, Agent, or Firm* — Norton Rose Fulbright US LLP

(57) ABSTRACT

The present invention relates to improved methods for producing adenovirus compositions wherein host cells are grown in a bioreactor and purified by size partitioning purification to provide purified adenovirus compositions.

28 Claims, 6 Drawing Sheets

(56) References Cited

FOREIGN PATENT DOCUMENTS

| WO | WO 98/26048 | 6/1998 |
|---|---|---|
| WO | WO 98/35554 | 8/1998 |
| WO | WO 99/12568 | 3/1999 |
| WO | WO 99/41416 | 8/1999 |
| WO | WO 99/43843 | 9/1999 |
| WO | WO 99/54441 | 10/1999 |
| WO | WO 00/34444 | 6/2000 |
| WO | WO 00/40702 | 7/2000 |
| WO | WO 02/29388 | 4/2002 |

OTHER PUBLICATIONS

Benvenisty and Neshif, "Direction introduction of genes into rats and expression of the genes," *Proc. Nat'l Acad. Sci. USA*, 83:9551-9555, 1986.

Berg et al., "High-level expression of secreted proteins from cells adapted to serum-free suspension culture," *BioTechniques*, 14(6):972-978, 1993.

Berg, "High-level expression of secreted proteins from cells adapted to serum-free suspension culture," *Biotechniques*, 14(6):972-978, 1993.

Bett, "An efficient and flexible system for construction of adenovirus vectors with insertions or deletions in early regions 1 and 3," *Proc. Natl. Acad. Sci. USA*, 91(19):8802-8806, 1994.

Blackwell et al., "High-level expression of secreted proteins from cells adapted to serum-free suspension culture," *Arch. Otolaryngol. Head Neck Surg.*, 125(8):856-863, 1999.

Brett et al., "Comparison of antigen presentation of influenza A nucleoprotein expressed in attenuated AroA- *Salmonella typhimurium* with that of live virus," *J. Immunol.*, 150:2869-2884, 1993.

Bussemakers et al., "Decreased expression of E-cadherin in the progression of rat prostatic cancer," *Cancer Res.*, 52:2916-2922, 1992.

Butman et al., "High Sensitivity HPLC Method for Determining Viral Particle Concentration," Presentation, 2000.

Caldas et al., "Frequent somatic mutations and homozygous deletions of the p16 (MTS1) gene in pancreatic adenocarcinoma," *Nat. Genet.*, 8:27-32, 1994.

Carrion et al., "Intrinsic Fluorescence of Adenovirus Type S: A Sensitive Detection Alternative," *Molecular Ther.*, 3:438, 2001.

Cartwright, "Fermenter design for animal cell cultures," Animal Cells as Bioreactors, Cambridge University Press, 58-63, 1994.

Carver et al., "Transgenic livestock as bioreactors: stable expression of human alpha-1-antitrypsin by a flock of sheep," *Biotechnology NY*, 11:1263-1270, 1993.

Casey et al., "Growth suppression of human breast cancer cells by the introduction of a wild-type p53 gene," *Oncogene*, 6:1791-1797, 1991.

Chen and Okayama, "High-efficiency transfection of mammalian cells by plasmid DNA," *Mol. Cell Biol.*, 7:2745-2752, 1987.

Cheng et al., "*p16* Alterations and deletion mapping of 9p21-p22 in malignant mesothelioma," Cancer Res., 54:5547-5551, 1994.

Cheung et al., "Structure and function of C-CAM1,"*J Biol Chem.* 268(32):24303-24310, 1993.

Cheung et al., "The cytoplaxmic domain of C-CAM is required for C-CAM-mediated adhesion function: studies of a C-CAM transcript containing an unspliced intron", *Biochem. J.*, 295:427-435, 1993.

Chillon et al., "Group D Adenoviruses Infect Primary Central Nervous System Cells More Efficiently than Those from Group C," *J. Virol.*, 73(3):2537-2570, 1999.

Chroboczek et al., "The sequence of the genome of adenovirus type 5 and its comparison with the genome of adenovirus type 2," *Virology*, 186:280-285, 1992.

Coffin, "Retroviridae and their replication," *In: Virology*, Fields et al. (eds.), New York: Raven Press, pp. 1437-1500, 1990.

Complaint *Aventis Pharmaceuticals Products Inc. and Aventis Pharma, S.A.*, Plaintiffs, v. *Introgen Therapeutics, Inc.*, Defendant. Civil Action No. 01-451 from the U.S. District Court for the District of Delaware, Jun. 29, 2001.

Corveleyn and Remon, "Maltodextrins as lyoprotectants in the lyophilization of a model protein, LDH," *Pharm. Res.*, 13:146-150, 1996.

Cote et al., "Study of adenovirus production in serum-free 293SF suspension culture by GFP-Expression monitoring," *Biotechnol. Prog.*, 1997, 13, 709-714, Biotechnology Research Institute, National Research Council Canada, 6100 Royalmount Avenue, Montreal, Quebec, Canada H4P 2R2, S8756-7938(97)00110-0 CCC, 1997 American Chemical Society and American Institute of Chemical Engineers.

Coupar et al., "A general method for the construction of recombinant vaccinia virus expressing multiple foreign genes," *Gene*, 68:1-10, 1988.

Cristiano et al., "Viral and nonviral gene delivery vectors for cancer gene therapy," *Cancer Detec. Prev.*, 22(5):445-454, 1998.

Crooks et al., "Purification and analysis of infectious virions and native non-structural antigens from cells infected with tick-borne encephalitis virus," *J. Chromatogr.*, 502(1):59-68, 1990.

Croyle et al., "Factors that influence stability of recombinant adenoviral preparations for human gene therapy," *Pharm. Dev. Technol.*, 3(3):373-383, 1998.

Declaration of Peter Clarke, Ph.D.; submitted in European Patent Application No. 97950677.1.

Dorai et al., "A recombinant defective adenoviral agent expressing anti-bcl-2 ribozyme promotes apoptosis of bcl-2-expressing human prostate cancer cells," *Int. J. Cancer*, 82(6):846-852, 1999.

Dubensky et al., "Direct transfection of viral and plasmid DNA into the liver or spleen of mice," *Proc. Nat. Acad. Sci. USA*, 81:7529-7533, 1984.

Edelman and Crossin, "Cell adhesion molecules: implications for a molecular histology," *Annu. Rev. Biochem.*, 60:155-190, 1991.

Edelman, "Cell adhesion and the molecular processes of morphogenesis," *Annu. Rev. Biochem.*, 54:135-169, 1985.

Fechheimer et al., "Transfection of mammalian cells with plasmid DNA by scrape loading and sonication loading," *Proc. Nat'l Acad. Sci. USA*, 84:8463-8467, 1987.

Ferkol et al., "Regulation of the phosphoenolpyruvate carboxykinase/human factor IX gene introduced into the livers of adult rats by receptor-mediated gene transfer, " *FASEB J.*, 7:1081-1091, 1993.

Fraley et al., "Entrapment of a bacterial plasmid in phospholipid vesicles: Potential for gene transfer," *Proc. Nat'l Acad Sci. USA*, 76:3348-3352, 1979.

Freshney, "Animal Cell Culture: a Practical Approach", Second Edition, Oxford/New York, IRL Press, Oxford University Press, 1992.

Fried and Bromberg, "Factors that affect the stability of protein-DNA complexes during gel electrophoresis," *Electrophoresis*, 18:6-11, 1997.

Frixen et at,"E-cadherin-mediated cell-cell adhesion prevents invasiveness of human carcinoma cells," *J. Cell Biol.*, 113:173-185, 1991.

Garnier et al., "Scale-up of the adenovirus expression system for the production of recombinant protein in human 293S cells," *Cytotechnology*, 15(1-3):145-155, 1994.

Gilbert, "Adaptation of cells to serum free culture for production of adenovirus vectors and recombinant proteins," *Williamsburg BioProcessing Conference*, Nov. 18-21, 1996.

Goldenstein et al., "Defective lipoprotein receptors and atherosclerosis. Lessons from an animal counterpart of familial hypercholesterolemia," *New Engl. J. Med.*, 309(11983):288-296, 1983.

Graham and Prevec, "Manipulation of adenovirus vectors," In: *Methods in Molecular Biology Gene Transfer and Expression Protocol*, Murray (Ed.), Humana Press, Clifton, NJ, 7:109-128, 1991.

Graham and Prevec, "Methods for construction of adenovirus vectors," *Mol. Biotechnol.*, 3(3):207-220, 1995.

Graham et al., "Characteristics of a human cell line transformed by DNA from human adenovirus type 5," *J. Gen. Virol.*, 36(1):59-74, 1977.

Graham, "Growth of 293 cells in suspension culture," *J. Gen. Virol.*, 68(Pt. 3):937-940, 1987.

(56) References Cited

OTHER PUBLICATIONS

Griffiths, "Overview of cell culture systems and their scale-up," In: Animal Cell Biotechnology, vol. 3, p. 179-220, (Spier and Griffiths, eds.), Academic Press, London, 1986.

Griffiths, "Quantitation in immunocytochemistry: correlation of immunogold labeling to absolute number of membrane antigens," J. Histochem. Cytochem., 34(11):1389-1398, 1986.

Hall et al., "Stabilizing effect of sucrose against irreversible denaturation of rabbit muscle lactate dehydrogenase," Biophys. Chem., 57:47-54, 1995.

Han et al., "Receptor-mediated gene transfer to cells of hepatic origin by galactosylated albumin-polylysine complexes," Biol. Pharm. Bull., 22(8):836-840, 1999.

Harland and Weintraub, "Translation of mammalian mRNA injected into Xenopus oocytes is specifically inhibited by antisense RNA," J. Cell Biol., 101:1094-1099, 1985.

Haruna et al., "Separation of adenovirus by chromatography on DEAE-Cellulose," Discussion and Preliminary Reports, pp. 264-267; Institute for Virus Research, Kyoto University, Kyoto, Japan—Sep. 22, 1960.

Hay et al., "Replication of adenovirus mini-chromosomes," J. Mol. Biol., 175:493-510, 1984.

Hearing and Shenk, "Functional analysis of the nucleotide sequence surrounding the cap site for adenovirus type 5 region E1A messenger RNAs," J. Mol. Biol., 167:809-822, 1983.

Hearing et al., "Identification of a repeated sequence element required for efficient encapsidation of the adenovirus type 5 chromosome," J. Virol., 61:2555-2558, 1987.

Herman et al., "The effect of bulking agent on the solid-state stability of freeze-dried methylprednisolone sodium succinate," Pharm. Res., 11:1467-1473, 1994.

Hermens and Verhaagen, "Viral vectors, tools for gene transfer in the nervous system," Prog. Neurobiol., 55(4):399-432, 1998.

Hermonat and Muzycska, "Use of adenoassociated virus as a mammalian DNA cloning vector: Transduction of neomycin resistance into mammalian tissue culture cells," Proc. Nat'l Acad. Sci. USA, 81:6466-6470, 1984.

Hollstein et al., "p53 mutations in human cancers," Science, 253(5015):49-53, 1991.

http://www.sterlich.com/generalfaq.htm.

Hurwitz et al., "Suicide gene therapy for treatment of retinoblastoma in a murine model," Human Gene Therapy, 10:441-448, 1999.

Hussussian et al., "Germline p16 mutations in familial melanoma," Nature Genetics, 8(1):15-21, 1994.

Huyghe et al., "Purification of a type 5 recombinant adenovirus encoding human p53 by col. chromatography," Human Gene Therapy, 6:1403-1416, 1996.

International Search Report, dated May 18, 2007, in corresponding International PCT Appli. No. PCT/US05/26178.

Irie et al., "Therapeutic efficacy of an adenovirus-mediated anti-H-ras ribozyme in experimental bladder cancer," Antisense Nucleic Acid Drug Dev., 9(4):341-349, 1999.

Ishibashi et al., "Hypercholesterolemia in low density lipoprotein receptor knockout mice and its reversal by adenovirus-mediated gene delivery," J. Clin. Invest., 92:883-893, 1993.

Ishibashi et al., "Massive xanthomatosis and atherosclerosis in cholesterol-fed low density lipoprotein receptor-negative mice," J. Clin. Invest., 93:1885-1893, 1994.

Jardon and Garnier, "PH, pCO2, and temperature effect on R-adenovirus production," Biotechnol. Prog., 19(1):202-208, 2003.

Jiang et al., "The melanoma differentiation associated gene mda-7 suppresses cancer cell growth," Proc. Nat'l. Acad. Sci. USA, 93:9160-9165, 1996.

Jones and Sheik, "Isolation of deletion and substitution mutants of adenovirus type 5," Cell, 13:181-188, 1978.

Jul. 17, 2006: Minutes of Oral Proceedings Before the Examining Division with decision to grant European Patent Application No. 97950677.1.

Kamb et al.," A cell cycle regulator potentially involved in genesisi of many tumor types," Science, 264:436-440, 1994.

Kamb et al., "Analysis of the p16 gene (CDKN2) as a candidate for the chromosome 9p melanoma susceptibility locus," Nature Genetics, 8:22-26, 1994.

Kaneda et al., "Increased expression of DNA cointroduced with nuclear protein in adult rat liver," Science, 243:375-378, 1989.

Kato et al., "Expression of hepatitis b virus surface antigen in adult rat liver," J. Biol. Chem., 266:3361-3364, 1991.

Klein et al., "High-velocity microprojectiles for delivering nucleic acids into living cells," Nature, 327:70-73, 1987.

Kotani et al., "Improved methods of retroviral vector transduction and production for gene therapy," Human Gene Therapy, 5:19-28, 1994.

Larsson and Litwin, "The growth of polio virus in human diploid fibroblasts grown with cellulose microcarriers in suspension cultures," Dev. Biol. Standard, 66:385-390, 1987.

Lentfer and Conde, "A rapid and inexpensive procedure for the purification of adenovirions," Archives of Virology, 56:189-193, 1978.

Lesch, "Gene transfer to the brain: emerging therapeutic strategy in psychiatry?," Biol. Psychiatry, 45(3):247-253, 1999.

Levrero et al., "Defective and nondefective adenovirus vectors for expressing foreign genes in vitro and in vivo," Gene, 101:195-202, 1991.

Lin and Guidotti, "Cloning and expression of a cDNA coding for a rat liver plasma membrane ecto-ATpase," J. Biol. Chem., 264:14408-14414, 1989.

Lu et al., "Coat protein interactions involved in tobacco mosaic tobamovirus cross-protection," Virology, 248:188-198, 1998.

Lueckel et al., "Formulations of sugars with amino acids or mannitol—influence of concentration ratio on the properties of the freeze-concentrate and the lyophilizate," Pharm. Dev. Technol., 3:326-336, 1998.

Mann et al., "Construction of a retrovirus packaging mutant and its use to produce helper-free defective retrovirus," Cell, 33:153-159, 1983.

Marienfeld et al.,"'Autoreplication' of the vector genome in recombinant adenoviral vectors with different E1 region deletions and transgenes," Gene Ther., 6(6):1101-1113, 1999.

Massie et al., "Improved adenovirus vector provides herpes simplex virus ribonucleotide reductase R1 and R2 subunits very efficiently," Biotechnology, vol. 13; 602-608, Jun. 1995, Institute of Research in Biotechnology, Montreal, Quebec, Canada H4P 2R2; Institute of Cancer of Montreal, Quebec, Canada H2I 4MI, 1995 Nature Publishing Group.

Matsuura et al., "Altered expression of e-cadherin in gastric cancer tissues and carcinomatous fluid," Brit. J. Cancer, 66:1122-1130, 1992.

McGrath et al., "Retrovirus purification: method that conserves envelope glycoprotein and maximizes infectivity," J. Virol., 25:923-927, 1978.

Mercer, "Cell cycle regulation and the p53 tumor suppressor protein," Critic. Rev. Eukar. Gene Express. 2:251-263, 1992.

Mincheff et al., "Naked DNA and adenoviral immunizations for immunotherapy of prostate cancer: a phase I/II clinical trial," Eur. Urol., 38(2):208-217, 2000.

Mizrahi, "Production of human interferons: an overview," Dev. Biol. Stand., 55:219-230, 1983.

Montagnon, "Polio and rabies vaccines produced in continuous cell lines: a reality for vero cell line," Develop. Biol. Standard., 70:27-47, 1989.

Mori et al., "Frequent somatic mutation of the MTSI/CDK4I (Multiple Tumor suppressor/Cyclin dependent Kinase 4 Inhibitor) gene in esophageal squamous cell carcinoma," Cancer Res., 54:3396-3397, 1994.

Morris et al., "Serum-free production of adenoviral vectors for gene therapy," Williamsburg BioProcessing Conference, Nov. 18-21, 1996.

Morris et al., "Cell cycle traverse in AHH-1 tk +/− human lymphoblastoid cells exposed to the chromosomal mutagen, m-amsa," Environ. Mol. Mutagen, 27(1):10-18, 1996.

(56) References Cited

OTHER PUBLICATIONS

Morrison et al., "Complete DNA sequence of canine adenovirus type 1," *J. Gen. Virol.*, 78(Pt. 4):873-878, 1997.
Murakami et al., "Quantitation of adenovirus DNA and virus particles with the PicoGreen fluorescent Dye," *Analytical Biochemistry*, 274:283-288, 1999.
Murphy et al., "Virus Taxonomy," In B.N. Fields et al., Fields Virology, 3$^{rd}$. ed., Philadelphia: Lippencott-Raven Publishers, Table 6, pp. 51-54, 1996.
Nadeau et al., "Improvement of recombinant protein production with the human adenovirus/293S expression system using Fed-Batch strategies," *Biotechnology and Bioengineering*, vol. 51, pp. 613-623, 1996, Jon Wiley & Sons, Inc.
Nicolas and Rubenstein, "Retroviral vectors," *In: Vectors: A Survey of Molecular Cloning Vectors and Their Uses*, Rodriguez and Denhardt, (eds.), Stoneham: Butterworth, Chapter 23, pp. 493-513, 1988.
Nicolau and Sene, "Liposome-mediated DNA transfer in eukaryotic cells," *Biochem. Biophys. Acta*, 721:185-190, 1982.
Nicolau et al., "Liposomes as carriers for *in vivo* gene transfer and expression," *Methods Erzyinol.*, 149:157-176, 1987.
Nilsson and Mosbach, "Immobilized animal cells," *Dev. Biol. Standard*, 66:183-193,.
Nobori et al., "Deletions of the cyclin-dependent kinase-4 inhibitor gene in multiple human cancers," *Nature*, 368:753-756, 1994.
O'Neil and Balkovic, "Virus harvesting and affinity-based liquid chromatography. A method for virus concentration and purification," *Biotechnology*, 11(2):173-178, 1993.
Obrink, "C-CAM (cell-CAM 105)—a member of the growing immunogloublin superfamily of cell adhesion proteins," *BioEssays*, 13:227-233, 1991.
Odin and Obrink, "Quantitative determination of the organ distribution of the cell adhesion molecule cell-CAM 105 by radioimmunoassay," *Exp. Cell Res.*, 171:1-15, 1987.
Office Communication, issued in U.S. Appl. No. 11/187,319, dated May 29, 2009.
Office Communication, issued in U.S. Appl. No. 11/187,319, dated Dec. 4, 2008.
Office Communication, issued in U.S. Appl. No. 11/187,319, dated Mar. 10, 2008.
Office Communication, issued in U.S. Appl. No. 11/187,319, dated May 3, 2007.
Office Communication, issued in U.S. Appl. No. 09/203,078, dated Oct. 19, 2005.
Office Communication, issued in U.S. Appl. No. 09/203,078, dated Nov. 17, 2004.
Office Communication, issued in U.S. Appl. No. 09/203,078, dated Jun. 3, 2004.
Office Communication, issued in U.S. Appl. No. 09/203,078, dated Oct. 3, 2003.
Office Communication, issued in U.S. Appl. No. 09/203,078, dated Sep. 13, 2001.
Office Communication, issued in U.S. Appl. No. 09/203,078, dated Mar. 20, 2001.
Office Communication, issued in U.S. Appl. No. 08/975,519, dated Sep. 23, 2009.
Office Communication, issued in U.S. Appl. No. 08/975,519, dated Jun. 24, 1999.
Office Communication, issued in U.S. Appl. No. 08/975,519, dated Sep. 25, 1998.
Okamoto et al., "Mutations and altered expression of p16$^{INK4}$ in human cancer," *Proc. Nat'l Acad. Sci. USA*, 91:11045-11049, 1994.
Orlow et al., "Chromosome 9 allelic losses and microsatellite alterations in human bladder tumors," *Cancer Res.*, 54:2848-2851, 1994.
Parks et al., "A helper-dependent system for adenovirus vector production helps define a lower limit for efficient DNA packaging," *J. Virol.*,71(4):3293-3298, 1997.
Paskind et al. ,"Dependence of moloney murine leukemia virus production on cell growth," *Virology*, 67:242-248, 1975.

Payment et al., In: *Biotechnology Current Progress*, ed. P.N. Cheremisinoff et al., Technomic Publishing, 1991.
Perales et al., "Gene transfer in vivo: sustained expression and regulation of genes introduced into the liver by receptor-targeted uptake, " *Proc. Natl. Acad. Sci. USA*, 91:4086-4090, 1994.
Perrin et al., "An experimental rabies vaccine produced with a new BHK-21 suspension cell culture process: use of serum-free medium and perfusion-reactor system," *Vaccine*, 13(13):1244-1250,1995.
Petricciani, "Should continuous cell lines be used as substrates for biological products?,"*Dev. Biol. Standard*, 66:3-12, 1985.
Petrof, "Respiratory muscles as a target for adenovirus-mediated gene therapy," *Eur. Respir. J.*, 11(2): 492-497, 1998.
Phillips et al., "Experience in the cultivation of mammalian cells on the 800 l scale," In: *Large Scale Mammalian Cell Culture* (Feder and Tolbert, Eds.) Academic Press, FL, 1985.
Potter et al., "Enhancer-dependent expression of human k immunoglobulin genes introduced into mouse pre-B lymphocytes by electroporation," *Proc. Nat'l Acad. Sci. USA*, 81:7161-7165, 1984.
Racher et al., "Culture of 293 cells in different culture systems: cell growth and recombinant adenovirus production," *Biotechnology Techniques*, 9:169-174, 1995.
Reddy et al., "Nucleotide sequence and transcription map of porcine adenovirus type 3," *Virology*, 251(2):414-26, 1998.
Renan, "Cancer genes: current status, future prospects, and applications in radiotherapy/oncology," *Radiother. Oncol.*, 19:197-218, 1990.
Ridgway, "Mammalian expression vectors," In: Rodriguez RL, Denhardt DT, ed. Vectors: A survey of molecular cloning vectors and their uses. Stoneham: Butterworth, pp. 467-492, 1988.
Rippe et al., "DNA-mediated gene transfer into adult rat hepatocytes in primary culture," *Mol. Cell Biol.*, 10:689-695, 1990.
Robbins and Ghivizzani, "Viral vectors for gene therapy," *Pharmacol. Ther.*, 80(1):35-47, 1998.
Robbins et al, "Viral vectors for gene therapy," *Trends Biotechnol.*, 16(1):35-40, 1998.
Roux et al., "A versatile and potentially general approach to the targeting of specific cell types by retroviruses: application to the infection of human cells by means of major histocompatibility complex class I and class II antigens by mouse ecotropic murine leukemia virus-derived viruses," *Proc. Nat'l Acad. Sci. USA*, 86:9079-9083, 1989.
Sagrera et al., "Study of the influence of salt concentration on Newcastle disease virus matrix protein aggregation,"*Biochem. Mol. Biol. Int.*, 46:429-435, 1998.
Serrano et al., "A New Regulatory Motif in Cell-Cycle Control Causing Specific Ihyibition of Cyclin D/CDK4," *Nature*, 366:704-707, 1993.
Serrano et al., "Inhibition of Ras-Induced Proliferation and Cellular Transformation by p16$^{INK}$4," *Science*, 267:249-252, 1995.
Shabram et al., "Analytical anion-exhange HPLC of recombinant type-5 adenoviral particles," *Human Gene Therapy*, 8:453-465, 1997.
Smith and Lee, "Large-scale isolation and partial purification of type C RNA viruses on hydroxyapatite. I. Biochemical characterization," *Anal. Biochem.*, 86(1):252-263, 1978.
Stewart et al., "Adenovector-mediated gene delivery of interleukin-2 in metastatic breast cancer and melanoma: results of a phase 1 clinical trial," *Gene Ther.*, 6(3):350-63, 1999.
Su et al., "Alterations in pancreatic, biliary, and breast carcinomas support MKK4 as a genetically targeted tumor suppressor gene," *Cancer Res.*, 58:2339-2342, 1998.
Takahasi et al., "Wild-type but not mutant p53 suppresses the growth of human lung cancer cells bearing multiple genetic lesions," *Cancer Res.*, 52:2340-2342, 1992.
Tanzawa et al., "WHHL-rabbit: a low density lipoprotein receptor-deficient animal model for familial hypercholesterolemia," *FEBS Letters*, 118(1):81-84, 1980.
Temin, "Retrovirus vectors for gene transfer: efficient integration into and expression of exogenous DNA in vertebrate cell genomes," *In: Gene Transfer*, (Kucherlapati, ed.), Plenum Press, New York, pp. 149-188, 1986.
Tibbetts, "Viral DNA sequences from incomplete particles of human adenovirus type 7," *Cell*, 12:243-249, 1977.

(56) References Cited

OTHER PUBLICATIONS

Trepanier et al., "Concentration of human respiratory syncytial virus using ammonium sulfate, polyethylene glycol or hollow fiber ultrafiltration," *Journal of Virological Methods*, 3:201-211, 1981.
Tur-Kaspa et al., "Use of electroporation to introduce biologically active foreign genes into primary rat hepatocytes," *Mol. Cell Biol.*, 6:716-718, 1986.
Umbas et al., "Expression of the cellular adhesion molecule E-cadherin is reduced or absent in high-grade prostate cancer," *Cancer Res.*, 52:5104-5109, 1992.
U.S. Appl. No. 60/026,667 entitled "Method for the Production of Recombinant Adenoviruses ," by , Jean-Mar. Guillaume, filed Sep. 25, 1996.
U.S. Appl. No. 60/082,628 entitled "Efficient Purification of Infectious Adenovirus," by , Miguel Carrion et al., filed Apr. 22, 1998.
Van Wezel, "Growth of cell-strains and primary cells on microcarriers in homogeneous culture," *Nature*, 216:64-65, 1967.
Vanderkwaak and Alvarez, "Immune directed therapy for ovarian carcinoma," *Curr. Opin. Obstet. Gynecol.*, 11(1):29-34, 1999.
Vanlandschoot et al., "pH-dependent aggregation and secretion of soluble monomeric influenza hemagglutinin," *Arch. Virol.*, 143:227-239, 1998.
Vossen and Fried, "Sequestration stabilizes lac repressor-DNA complexes during gel electrophoresis," *Anal. Biochem.*, 245:85-92, 1997.
Wagner et al., "Antisense gene inhibition by oligonucleotides containing C-5 propyne pyrimidines," *Science*, 260:1510-1513, 1993.
Wagner et al., "Transferrin-polycation conjugates as carriers for DNA uptake into cells", *Proc. Nat'l. Acad. Sci.*, 87(9):3410-3414, 1990.
Wang et al., "High cell density perfusion culture of hybridoma cells for production of monoclonal antibodies in the celligen packed bed reactor," In: *Animal Cell Technology: Basic and Applied Aspects*, Kaminogawa et al., (Eds.), 5:463-469, Kluwer Academic Publishers, Netherlands, 1993.
Wang et al., "Modified CelliGen-packed bed bioreactors for hybridoma cell cultures," *Cytotechnology*, 9:41-49, 1992.
Wang et al., In: *Animal Cell Technology: Basic and Applied Aspects*, Kobayashi et al., (Eds.), 6:115-120, Kluwer Academic Publishers, Netherlands, 1994.
Watanabe, "Serial inbreeding of rabbits with hereditary hyperlipidemia (WHHL-rabbit)," *Atherosclerosis*, 36:261-268, 1980.
Watt et al.,"Human prostate-specific antigen: structural and functional similarity with serine proteases", *Proc. Nat'l Acad. Sci.*, 83(2):3166-3170, 1986.
Weinberg, "Tumor suppressor genes," *Science*, 254(5035):1138-1146, 1991.
Wills and Menzel, "Adenovirus Vectors for Gene Therapy of Cancer," *J. of Cellular Biochem.*, Suppl: 17E, S216:206, 1993.
Wilson, "Cystic fibrosis. Vehicles for gene therapy," *Nature*, 365:691-692, 1993.
Wilson, "When bad gene transfer is good," *J. Clin. Invest.*, 98(11):2435, 1996.
Written Opinion, dated May 18, 2007, in corresponding International PCT Appl. No. PCT/US05/26178.
Wu and Wu, "Evidence for targeted gene delivery to HepG2 hepatoma cells *in vitro,*" *Biochemistry*, 27:887-892, 1988.
Wu and Wu, "Liver-directed gene delivery", *Adv. Drug Delivery Rev.*, 12:159-167, 1993.
Wu and Wu, "Receptor mediated in vitro gene transfections by a soluble DNA courier system," *J. Biol. Chem*, 262:4429-4432, 1987.
Yang et al., "In vivo and in vitro gene transfer to mammalian somatic cells by particle bombardment," *Proc. Nat'l Acad. Sci. USA*, 87:9568-9572, 1990.
Yotnda et al., "Efficient infection of primitive hematopoietic stem cells by modified adenovirus," *Gene Ther.*, 8:930-937, 2001.
Zhang et al., "Adenovirus inhibition of cell translation facilitates release of virus particles and enhances degradation of the cytokeratin network," *Journal of Virology*, Apr. 1994, P. 2544-2555, 00022-538X/94, 1994 American Society for Microbiology, Department of Biochemistry and Kaplan Cancer Center, New York University School of Medicine, New York, New York 10016.
Zheng et al., "Transcription units of Ela, Elb and pIX regions of bovine adenovirus type 3," *J. Gen. Virol.*, 80 (Pt. 7):1735-1742, 1999.

* cited by examiner

METHOD FOR THE PRODUCTION AND PURIFICATION OF ADENOVIRAL VECTORS

CROSS REFERENCE TO RELATED APPLICATIONS

The present application is a continuation of U.S. patent application Ser. No. 11/187,319, filed Jul. 22, 2005 now abandoned, which claims benefit of U.S. Provisional Application Ser. No. 60/624,627 filed Nov. 3, 2004. The present application further is a continuation-in-part of U.S. patent application Ser. No. 09/203,078, filed Dec. 1, 1998 now U.S. Pat. No. 7,732,129. The entire text of each of the above-referenced disclosures are specifically incorporated by reference herein without disclaimer.

BACKGROUND OF THE INVENTION

1. Field of the Invention

The present invention relates generally to the fields of cell culture and virus production. More particularly, it concerns improved methods for the culturing of mammalian cells, infection of those cells with adenovirus and the production of infectious adenovirus particles therefrom.

2. Description of Related Art

A variety of cancer and genetic diseases currently are being addressed by gene therapy. Viruses are highly efficient at nucleic acid delivery to specific cell types, while often avoiding detection by the infected host's immune system. These features make certain viruses attractive candidates as gene-delivery vehicles for use in gene therapies (Robbins and Ghivizzani, 1998; Cristiano et al., 1998). Modified adenoviruses that are replication incompetent and therefore non-pathogenic are being used as vehicles to deliver therapeutic genes for a number of metabolic and oncologic disorders. These adenoviral vectors may be particularly suitable for disorders such as cancer that would best be treated by transient therapeutic gene expression since the DNA is not integrated into the host genome and the transgene expression is limited. Adenoviral vector may also be of significant benefit in gene replacement therapies, wherein a genetic or metabolic defect or deficiency is remedied by providing for expression of a replacement gene encoding a product that remedies the defect or deficiency.

Adenoviruses can be modified to efficiently deliver a therapeutic or reporter transgene to a variety of cell types. Recombinant adenoviruses types 2 and 5 (Ad2 and AdV5, respectively), which cause respiratory disease in humans, are among those currently being developed for gene therapy. Both Ad2 and AdV5 belong to a subclass of adenovirus that is not associated with human malignancies. Recently, the hybrid adenoviral vector AdV5/F35 has been developed and proven of great interest in gene therapies and related studies (Yotnda et al., 2001).

Recombinant adenoviruses are capable of providing extremely high levels of transgene delivery. The efficacy of this system in delivering a therapeutic transgene in vivo that complements a genetic imbalance has been demonstrated in animal models of various disorders (Watanabe, 1986; Tanzawa et al., 1980; Golasten et al., 1983; Ishibashi et al, 1993; and S. Ishibashi et al., 1994). Indeed, a recombinant replication defective adenovirus encoding a cDNA for the cystic fibrosis transmembrane regulator (CFTR) has been approved for use in at least two human CF clinical trials (Wilson, 1993). Hurwitz, et al., (1999) have shown the therapeutic effectiveness of adenoviral mediated gene therapy in a murine model of cancer (retinoblastoma).

As the clinical trials progress, the demand for clinical grade adenoviral vectors is increasing dramatically. The projected annual demand for a 300 patient clinical trial could reach approximately $6 \times 10^{14}$ PFU.

Traditionally, adenoviruses are produced in commercially available tissue culture flasks or "cellfactories." Adenoviral vector production has generally been performed in culture devices that supply culture surfaces for attachment of the HEK293 cells, such as 1-flasks. Virus infected cells are harvested and freeze-thawed to release the viruses from the cells in the form of crude cell lysate. The produced crude cell lysate (CCL) is then purified by double CsC1 gradient ultracentrifugation. The typically reported virus yield from 100 single tray cellfactories is about $6 \times 10^{12}$ PFU. Clearly, it becomes unfeasible to produce the required amount of virus using this traditional process. New scaleable and validatable production and purification processes have to be developed to meet the increasing demand.

The purification throughput of CsC1 gradient ultracentrifugation is so limited that it cannot meet the demand for adenoviral vectors for gene therapy applications. Therefore, in order to achieve large scale adenoviral vector production, purification methods other than CsC1 gradient ultracentrifugation have to be developed. Reports on the chromatographic purification of viruses are very limited, despite the wide application of chromatography for the purification of recbinant proteins. Size exclusion, ion exchange and affinity chromatography have been evaluated for the purification of retroviruses, tick-borne encephalitis virus, and plant viruses with varying degrees of success (Crooks, et al., 1990; Aboud, et al., 1982; McGrath et al., 1978, Smith and Lee, 1978; O'Neil and Balkovic, 1993). Even less research has been done on the chromatographic purification of adenovirus. This lack of research activity may be partially attributable to the existence of the effective, albeit non-scalable, CsC1 gradient ultracentrifugation purification method for adenoviruses.

Recently, Huyghe et al. (1996) reported adenoviral vector purification using ion exchange chromatography in conjunction with metal chelate affinity chromatography. Virus purity similar to that from CsC1 gradient ultracentrifugation was reported. Unfortunately, only 23% of virus was recovered after the double column purification process. Process factors that contribute to this low virus recovery are the freeze/thaw step utilized by the authors to lyse cells in order to release the virus from the c ells and the two column purification procedure. Of interest to the present invention is the disclosure of co-owned U.S. Published Patent Application No. 2004/0106184 A1, the disclosure of which is hereby incorporated by reference which is directed to methods for passing adenovirus particle preparations through chromatographic media to provide purified adenovirus particles.

For most of the E1 deleted first generation adenoviral vectors, production is carried out using HEK293 (human embryonal kidney cells, Invitrogen Corp.) cells which complement the adenoviral vector E1 deletion in trans. Because of the anchorage dependency of the HEK293 cells, adenoviral vector production has generally been performed in culture devices that supply culture surfaces for attachment of the HEK293 cells, such as T-flasks, multilayer Cellfactories™, and the large scale CellCube™ bioreactor system. Recently, the 11EK293 cells have been adapted to suspension culture in a variety of serum free media allowing production of adenoviral vectors in suspension bioreactors. Complete medium exchange at the time of virus infection using centrifugation is difficult to perform on a large scale. In addition, the shear stress associated with medium recirculation required for external filtration devices is likely to have a detrimental effect on host cells in a protein-free medium.

Of interest to the present invention are the disclosures of co-owned U.S. Pat. No. 6,194,191 and co-owned U.S. Pat. No. 6,726,907 the disclosures of which are hereby incorporated by reference, which are directed to improved Ad-p53 production methods with cells grown in serum-free conditions, and in particular in serum-free suspension culture. Also of interest to the present invention is the disclosure of WO 00/32754 based on U.S. Ser. No. 09/203,078, the disclosure of which is hereby incorporated by reference, which is directed to the use of low-medium perfusion rates in an attached cell culture system.

Clearly, there is a demand for improved methods of adenoviral vector production that will recover a high yield of product to meet the ever increasing demand for such products. Improved methods for adenoviral vector production can include improved techniques to make production more efficient, or optimization of operating conditions to increase adenoviral vector production.

SUMMARY OF THE INVENTION

The present invention is related to methods for producing purified viral compositions including adenovirus compositions of sufficient purity for therapeutic administration without the necessity for elaborate purification steps. More specifically, the invention relates to the discovery that size partitioning purification techniques may be used to provide adenoviral preparations of sufficient purity that they may be therapeutically administered without additional purification steps such as chromatographic and other methods previously considered necessary. Without intending to be bound by any particular theory of the invention it is believed that the steps of processing viral host cells in a cell suspension culture in a serum free media results in a viral particle product with a reduced load of contaminants. Moreover, the contaminants are of a size and nature that they may be readily separated from viral particles by a simple size partitioning purification step.

The ability to produce purified adenoviral preparations without traditional chromatographic purification steps provides significant improvements in viral production yields while reducing expense.

Specifically, the invention provides a method for removing contaminants from a virus-containing composition comprising obtaining an aqueous composition comprising a selected virus and undesirable contaminants and subjecting the aqueous composition to size partitioning purification using a size partitioning membrane having partitioning pores that retain virus and permit the passage of contaminants therethrough to remove contaminants and thereby provide a purified virus composition. Of course, the size of the partitioning pores will preferably be selected on the basis of the size of the virus that is to be retained, in which case one will select a membrane having a pore or inclusion size sufficiently smaller than the virus so as to retain the virus and yet permit the passage of contaminants. Similarly, if the pore or inclusion size is too small, some undesirable contaminants may be retained. Therefore, an optimal pore size is one that retains the most virus yet permits the passage of the most contaminants. Generally, the size of the virus and corresponding proposed preferred pore sizes will be as in Table 1 below:

TABLE 1

| Virus | Average Particle Size | Preferred Pore Size Range |
|---|---|---|
| Adenovirus | 80 nm | ≤0.05 µm |
| AAV | 20 nm | ≤0.01 µm |
| Retroviruses | 100 nm | ≤0.05 µm |
| Herpes virus | 100 nm | ≤0.05 µm |
| Lentivirus | 100 nm | ≤0.05 µm |

In particular embodiments, the invention provides a method of producing purified adenovirus composition comprising the steps of a) growing host cells in a medium; b) providing nutrients to said host cells; c) infecting said host cells with an adenovirus; d) lysing said host cells to provide a cell lysate comprising adenovirus; and e) purifying adenovirus from said lysate by size partitioning purification utilizing 15 a size partitioning membrane to provide a purified adenovirus composition.

The methods of the invention may be used when the virus is adenovirus, lentivirus, adenoassociated virus, retrovirus or herpes virus.

Particularly preferred methods of the invention are those in which the size partitioning membrane is in a tangential flow filtration device.

According to one aspect of the invention the size partitioning membrane is a porous filter. More specifically, the size partitioning membrane may be a dialysis membrane. The size partitioning membrane preferably has a pore size of less than about 0.08 microns and greater than about 0.0001 microns. Size partitioning membranes having pore sizes less than 0.05 microns and greater than 0.0001 microns 25 and those having pore sizes less than 0.02 microns and greater than 0.0001 microns are particularly preferred. For viruses such as adeno-associated virus (AAV) a pore size of less than 0.01 microns but greater than 0.0001 microns is preferred.

According to one aspect of the invention, the size partitioning purification could be carried out by gel filtration purification. Such a method is not preferred, however, because get filtration size partitioning effects a dramatic increase in volume and dilutes the viral preparation. Such diluted preparations must then be reconcentrated which is costly and undesirable.

According to one aspect of the invention virus may be purified to a pharmaceutically acceptable degree without the use of additional purification steps such as ion exchange chromatography. By pharmaceutically acceptable degree is meant substantially free of animal derived components and free of other protein impurities as seen on an SDS-PAGE gel so as to not impact on the human clinical use of the product. As another aspect of the invention, the purified adenovirus composition has a purity of less than 10 nanograms of contaminating DNA per 1 milliliter dose.

According to a preferred aspect of the invention at least $5\times10^{15}$ viral particles and more preferably $1\times10^{16}$ viral particles are obtained from a single culture preparation.

The host cells are preferably capable of growing in serum-free media and are grown in a serum-free medium. According to this method, the host cells may be adapted for growth in serum-free media by a sequential decrease in the fetal bovine serum content of the growth media. Preferred host cells are HEK293 cells. The host cells may be grown at least part of the time in a perfusion chamber, a bioreactor, a flexible bed platform or by fed batch. According to one method, the cells are perfused with a glucose containing media at a rate to provide a glucose concentration higher than 0.5 g/L with perfusion at a rate to provide a glucose concentration of between about 0.7 and 1.7 g/L being particularly preferred. The cells may be grown as a cell suspension culture or alternatively as an anchorage-dependent culture.

Lysis of the host cells may be carried out by a process that includes hypotonic solution, hypertonic solution, impinging jet, microfluidization, solid shear, detergent, liquid shear, high pressure extrusion, autolysis or sonication. Suitable detergents include those commercially available as Thesit®, NP-40®, Tween-20®, Brij-58®, Triton X-100® and octyl glucoside. According to one aspect of the invention the detergent is present in the lysis solution at a concentration of about 1% (w/v). The cell lysate may then be treated with a nuclease such as those available commercially as Benzonase® or Pulmozym®.

According to one aspect of the invention the viral particles are intended for use in gene therapy. Accordingly, the viral particle is an adenovirus which comprises an adenoviral vector encoding an exogenous gene construct. According to a further aspect of the invention the gene construct is operatively linked to a promoter. Suitable promoters include those selected from the group consisting of SV401E, RSV LTR, 13-actin, CMV IE, adenovirus major late, polyoma F9-1, or tyrosinase.

The exogenous gene construct can encode a therapeutic gene. Such genes are known to those of skill in the art and include, but are not limited to, those which encode antisense ras, antisense myc, antisense raf, antisense erb, antisense src, antisense fms, antisense jun, antisense trk, antisense ret, antisense gsp, antisense hst, antisense bcl antisense abl, Rb, CFTR, p16, p21, p27, p57, p'73, C-CAM, APC, CTS-1, zacl, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF G-CSF, thymidine kinase and p53.

Preferred viral vectors include adenoviral vectors- and particularly those in which the adenovirus is a replication-incompetent adenovirus. Such replication incompetent adenoviral vectors include those in which the adenovirus is lacking at least a portion of the E1-region with those lacking at least a portion of the E1A and/or E1B region being particularly preferred. According to one method, a replication incompetent adenovirus is produced in host cells which are capable of complementing replication. The present invention describes a new process for the production and purification of adenovirus. This new production process offers not only scalability and validatability but also excellent virus purity.

In preferred embodiments of the present invention, the adenovirus comprises an adenoviral vector encoding an exogenous gene construct. In certain such embodiments, the gene construct is operatively linked to a promoter. In particular embodiments, the promoter is SV40 1E, RSV LTR, B-actin or CMV 1E, adenovirus major late, polyoma F9-1, or tyrosinase. In particular embodiments of the present invention, the adenovirus is a replication-incompetent adenovirus. In other embodiments, the adenovirus is lacking at least a portion of the E1-region. In certain aspects, the adenovirus is lacking at least a portion of the E1A and/or E1B region. In other embodiments, the host cells are capable of complementing replication. In particularly preferred embodiments, the host cells are HEK293 cells.

In a preferred embodiment of the invention it is contemplated that the exogenous gene construct encodes a therapeutic gene. For example, the therapeutic gene may encode antisense ras, antisense myc, antisense raf, antisense erb, antisense src, antisense fms, antisense jun, antisense trk antisense ret, antisense gsp, antisense hst, antisense bcl antisense abl, Rb, CFTR, p16, p21, p27, p57, p73, C-CAM, APC, CTS-1, zacl, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11, IL-12, GM-CSF G-CSF, thymidine kinase or p53.

In certain aspects of the present invention, the cells may be harvested and lysed ex situ using a hypotonic solution, hypertonic solution, freeze-thaw, sonication, impinging jet, microfluidization or a detergent. In other aspects, the cells are harvested and lysed in situ using a hypotonic solution, hypertonic solution, or a detergent. As used herein the term "in situ" refers to the cells being located within the tissue culture apparatus for example CellCube™ and "ex situ" refers to the cells being removed from the tissue culture apparatus.

In particular embodiments, the cells are lysed and harvested using detergent. In preferred embodiments the detergent may be Thesit®, NP-406, Tween-206, Brij-58®, Triton X0-100 or octyl glucoside. In other aspects of the present invention lysis is achieved through autolysis of infected cells. In more particular embodiments the detergent is present in the lysis solution at a concentration of about 1% (w/v). In certain other aspects of the present invention the cell lysate is treated with Benzonase®, or Pulmozyme®.

In particular embodiments, the method further comprises a concentration step employing membrane filtration. In particular embodiments, the filtration is tangential flow filtration. In preferred embodiments, the filtration may utilize a 100 to 1000K NMWC, regenerated cellulose, or polyether sulfone membrane.

The present invention also provides an adenovirus produced according to a process comprising the steps of growing host cells in media, infecting the host cells with an adenovirus, harvesting and lysing the host cells to produce a crude cell lysate, concentrating the crude cell lysate, exchanging buffer of crude cell lysate, and reducing the concentration of contaminating nucleic acids in the crude cell lysate.

In yet another embodiment, the present invention provides a method for the purification of an adenovirus comprising the steps of growing host cells in serum-free media; infecting said host cells with an adenovirus; harvesting and lysing said host cells to produce a crude cell lysate; concentrating said crude cell lysate; exchanging buffer of crude cell lysate; and reducing the concentration of contaminating nucleic acids in said crude cell lysate. In preferred embodiments, the cells may be grown independently as a cell suspension culture or as an anchorage-dependent culture.

In particular embodiments, the host cells are adapted for growth in serum-free media. In more preferred embodiments, the adaptation for growth in serum-free media comprises a sequential decrease in the fetal bovine serum content of the growth media. More particularly, the serum-free media comprises a fetal bovine serum content of less than 0.03% v/v.

Also contemplated by the present invention is an adenovirus produced according to a process comprising the steps of growing host cells in serum-free media; infecting said host cells with an adenovirus; harvesting and lysing said host cells to produce a crude cell lysate; concentrating said crude cell lysate; exchanging buffer of crude cell lysate; and reducing the concentration of contaminating nucleic acids in said crude cell lysate.

The present invention further provides a 293 host cell adapted for growth in serum-free media. In certain aspects, the adaptation for growth in serum-free media comprises a sequential decrease in the fetal bovine serum content of the growth media. In particular embodiments, the cell is adapted for growth in suspension culture. In particular embodiments, the cells of the present invention are designated IT293SF cells. These cells were deposited with the American Tissue Culture Collection (ATCC) in order to meet the requirements of the Budapest Treaty on the international recognition of deposits of microorganisms for the purposes of patent procedure. The cells were deposited by Dr. Shuyuan Zhang on behalf of Introgen Therapeutics, Inc. (Houston, Tex.), on Nov. 17, 1997. IT293SF cell line is derived from an adaptation of 293 cell line into serum free suspension culture as described herein. The cells may be cultured in IS 293 serum-free media (Irvine Scientific. Santa Ma, Calif.) supplemented with 100 mg/L heparin and 0.1% Puronic F-68, and are permissive to human adenovirus infection.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

Other embodiments of the present invention pertain to methods for producing an adenovirus, including: (1) preparing an adenovirus preparation, including the steps of growing host cells in media in a bioreactor and initiating virus infection by diluting the host cells with fresh media and adenovirus; and (2) isolating adenovirus from the adenovirus preparation. Any bioreactor known to those of skill in the art that is capable of supporting host cell growth is contemplated for use in the present invention. A detailed discussion of various types of bioreactors is presented below in other parts of the specification.

According to one aspect of the present invention serum-free media is preferred for use in conjunction with the bioreactor, as long as the media is capable of supporting cell growth in the bioreactor. In other embodiments, the media is protein-free media. In some embodiments, the media is CD293 media medium (Invitrogen Corp.). In the embodiments of the present invention, the host cells may be grown in an anchorage-dependent culture or a non-anchorage-dependent (suspension) culture.

In the embodiments of the present invention that pertain to methods of producing an adenovirus which require a bioreactor, any bioreactor known to those of skill in the art is contemplated by the present invention. In certain embodiments, for example, the bioreactor comprises a bioreactor that uses axial rocking of a planar platform to induce wave motions inside of the bioreactor. In some embodiments, wave motions are induced inside of a sterilized polyethylene bag wherein the host cells are located. In further embodiments, the bioreactor is a disposable bioreactor. Any size of bioreactor is contemplated by the present invention. For example, the bioreactor may be a 10 L, a 20 L up to 200 L or larger bioreactor. In addition, the bioreactor may be a commercially-available bioreactor. For example, the bioreactor may be a Wave Bioreactor® (Wave Biotech, LLC, Bedminster, N.J.). According to one aspect of the invention a 20 L Wave Bioreactor® with an 8 L working volume may be used to culture adenoviral vectors transformed with the native p53 gene. The culture may be harvested on day 2 post infection using Tweene-20 to produce a yield of $2.3 \times 10^{11}$ viral particles/mL or 230,000 viral particles/cell. At such yields a 200 L bioreactor would be expected to yield approaching $2 \times 10^{16}$ VP.

In the embodiments of the present invention that pertain to methods of producing an adenovirus, it is contemplated that the operating conditions of the cell culture may be monitored or measured by any technique known to those of skill in the art. Examples of such conditions which may be monitored include pH of the media and dissolved oxygen tension of the media.

In the embodiments of the present invention that pertain to methods of producing an adenovirus, it is contemplated that the operating conditions of the cell culture may be monitored or measured by any technique known to those of skill in the art. Examples of such conditions which may be monitored include pH of the media and dissolved oxygen tension of the media.

Some embodiments of the present invention pertaining to methods of producing an adenovirus also involve processing and treating the media by any method known to those of skill in the art. For example, in certain embodiments of the present invention, the methods for producing an adenovirus involve perfusing the media through a filter. The filter may be a filter that is internal to the bioreactor system, or the filter may be incorporated so that it is external to the bioreactor. In certain embodiments, the filter is a floating flat filter. The floating flat filter may be used to remove spent media from the bioreactor. Any method known to those of skill in the art may be used to monitor and maintain media volume. In some embodiments, culture volume is maintained by a load cell used to trigger fresh media addition.

In embodiments of the present invention, media may or may not be perfused into the culture of host cells. In some embodiments of the present invention, media is perfused beginning on day 3 of host cell growth. One of skill in the art would be familiar with the wide range of techniques and apparatus available for perfusing media into a cell culture system.

In embodiments of the present invention that pertain to methods of producing an adenovirus, the step of diluting host cells with fresh media may be combined with the adenovirus infection step. This is based on the inventors' discovery that these two steps can be efficiently combined to provide for excellent yields of adenoviral vectors. The invention contemplates use of any method of dilution known to those of skill in the art. In certain embodiments, the host cells are diluted 2-fold to 50-fold with fresh media and adenovirus. In other embodiments, the host cells are diluted 10-fold with fresh media and adenovirus.

In the embodiments of the present invention that pertain to methods of producing an adenovirus, the initiating of virus infection of the host cells may be accomplished by any method known to those of skill in the art. For example, in embodiments of the present invention that involve use of bioreactors, the virus infection may take place in a second bioreactor. For example, virus infection of host cells may be accomplished by adding 20-100 vp/host cell. In certain other embodiments, virus infection involves adding about 50 vp/host cell. Virus infection may be allowed to proceed for any duration of time. One of skill in the art would be familiar with techniques pertaining to monitoring the progress of virus infection. In certain embodiments of the present invention, virus infection is allowed to proceed for about 4 days.

In certain other embodiments of the present invention, the isolating of the adenovirus from the adenovirus preparation occurs at about 4 days after viral infection is completed.

In the embodiments of the present invention that involve production of adenovirus, use of host cells is contemplated. Any cell type can be used as a host cell, as long as the cell is capable of supporting replication of adenovirus. One of skill in the art would be familiar with the wide range of host cells that can be used in the production of adenovirus from host cells. For example, in some embodiments of the present invention, the host cells complement the growth of the replication-deficient adenovirus. The replication-deficient adenovirus may be an adenovirus that lacks at least a portion of the E1-region, or it may be an adenovirus that lacks at least a portion of the E1A and/or E1B region. The host cells, for example, may be 293, HEK293, PER.C6, 911, and IT293SF cells. In certain embodiments of the present invention, the host cells are HEK293 cells.

In some embodiments of the present invention, the adenovirus is a recombinant adenovirus. For example, the recombinant adenovirus may encode a recombinant gene that is operatively linked to a promoter. Any promoter known to those of skill in the art can be used, as long as the promoter is capable of functioning as a promoter. For example, in certain embodiments the promoter is an SV40 E1, RSV LTR, /β-actin, CMV-IE, adenovirus major late, polyoma F9-1, or tyrosinase promoter.

In embodiments of the present invention where the adenovirus is an adenovirus encoding a recombinant gene, any recombinant gene, particularly a therapeutic gene, is contemplated by the present invention. For example, the recombinant gene may be selected from the group consisting of antisense ras, antisense myc, antisense raf antisense erb, antisense src, antisense fms, antisense jun, antisense ti-k, antisense ret, antisense gsp, antisense hst, antisense bcl antisense abl, Rb, CFTR, p16, p21, p27, p57, p73, C-CAM, APC, CTS-1, zacl, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferonβ, interferonγ, ADP (adenoviral death protein), or p53. In some embodiments, the recombinant gene is a p53 gene. In other embodiments, the recombinant gene is a mda-7 gene.

In some embodiments of the present invention, the recombinant gene is antisense ras, antisense myc, antisense raf antisense erb, antisense src, antisense fms, antisense jun, antisense trk, antisense ret, antisense gsp, antisense hst, antisense bcl antisense abl, Rb, CFTR, p16, p21, p27, p57, p73, C-CAM, APC, CTS-1, zacl, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, RaplA, cytosine deaminase, Fab, ScFv, BRCA2, zacl, ATM, HIC-1, DPC-4, FHIT, PTEN, ING1, NOEY1, NOEY2, OVCA1, MADR2, 53BP2, IRF-1, Rb, zacl, DBCCR-1, rks-3, COX-1, TFPI, PGS, Dp, E2F, ras, myc, neu, raf erb, fms, trk, ret, gsp, hst, abl, E1A, p300, VEGF, FGF, thrombospondin, BAI-1, GDAIF, or MCC.

In further embodiments of the present invention, the recombinant gene is a gene encoding an ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidease, a pullanase, a recombinase, a reverse transcriptase, a topoisomerase, a xylanase, a reporter gene, an interleukin, or a cytokine.

In other embodiments of the present invention, the recombinant gene is a gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione beta-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, beta-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase. Alternatively, the recombinant gene may encode growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, alpha melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

Certain of the embodiments of the present invention pertain to methods of producing an adenovirus that involve isolating the adenovirus from an adenovirus preparation. Any method of isolating the adenovirus from the adenovirus preparation known to those of skill in the art is contemplated by the present invention. In certain embodiments of the present invention, the host cells are harvested following infection but prior to lysis by the adenovirus, and lysing the host cells is performed by freeze-thaw, autolysis, or detergent lysis. In certain other embodiments of the present invention, the methods of producing adenovirus involve reducing the concentration of contaminating nucleic acids in the adenovirus preparation.

In some embodiments of the invention, the adenovirus that is isolated is placed into a pharmaceutically acceptable composition. One of skill in the art would be familiar with the extensive methods and techniques employed in preparing pharmaceutically acceptable compositions. Any pharmaceutical composition into which adenovirus can be formulated is contemplated by the present invention. For example, certain embodiments of the invention pertain to pharmaceutical preparation of adenovirus for oral administration, topical administration, or intravenous administration.

Some embodiments of the present invention involve analysis of virus production. For example, virus production may be analyzed using HPLC. Any technique for analyzing virus production known to those of skill is contemplated by the present invention.

In some embodiments of the invention, the methods for producing an adenovirus disclosed above and elsewhere in this specification concern methods for isolating and purifying an adenovirus that involve obtaining a purified adenovirus composition having one or more of the following properties: (1) a virus titer of between $1 \times 10^9$ and about $1 \times 10^{13}$ pfu/ml; (2) a virus particle concentration between about $1 \times 10^{10}$ and about $2 \times 10^{13}$ particles/ml; (3) a particle:pfu ratio between about 10 and about 60; (4) having less than 50 ng BSA per $1 \times 10^{12}$ viral particles; (5) between about 50 pg and 1 ng of contaminating human DNA per $1 \times 10^{12}$ viral particles; (6) a single HPLC elution peak consisting essentially of 97% to 100% of the area under the peak. In certain embodiments, the adenovirus composition prepared in accordance with the steps discussed above includes between $5 \times 10^{14}$ and $1 \times 10^{18}$ viral particles. In other embodiments, the composition is a pharmaceutically-acceptable composition.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
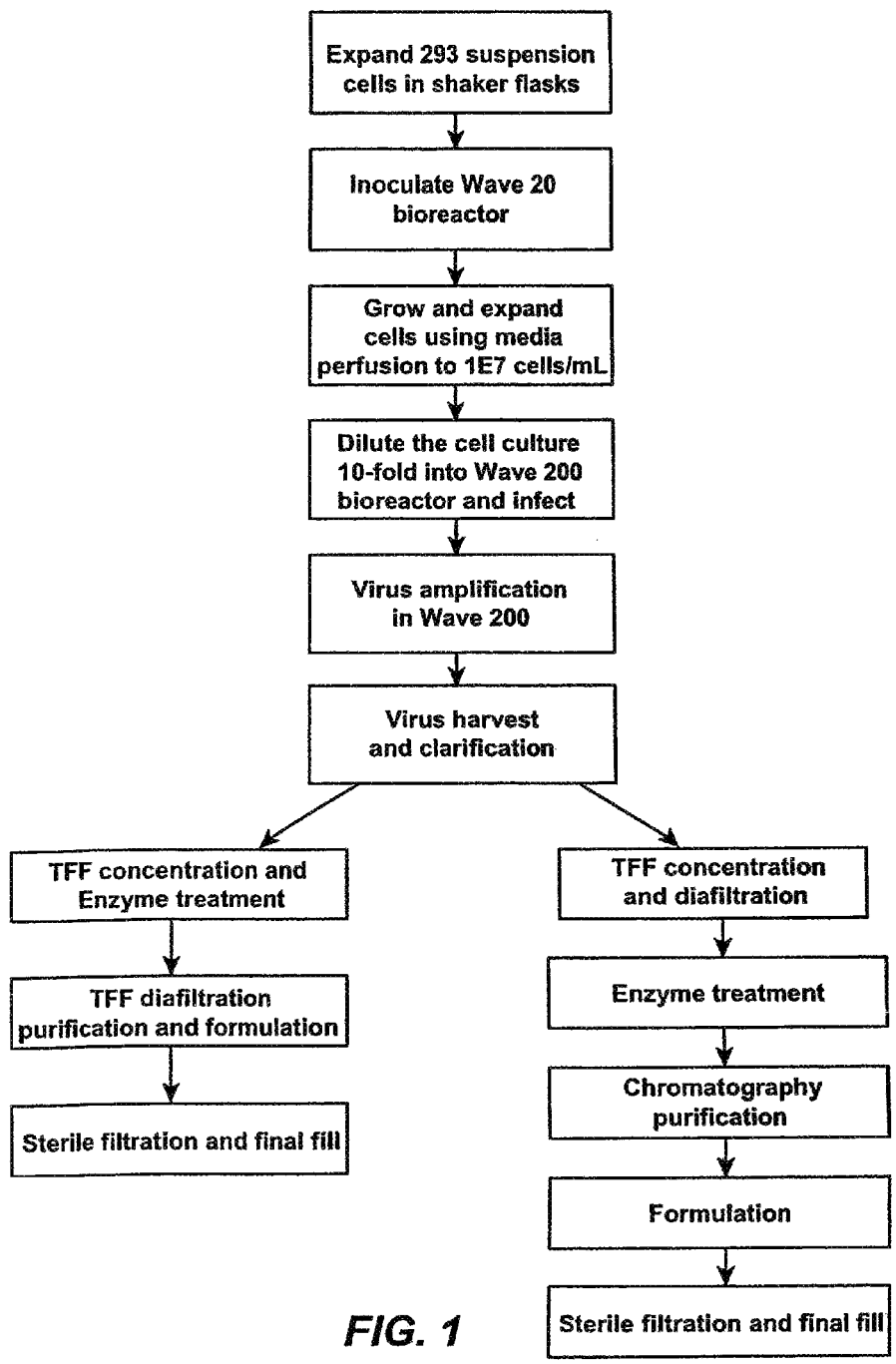
FIG. 1 depicts a production and purification flow chart for adenovirus using tangential flow filtration (TFF) diafiltration alone and TFF diafiltration in conjunction with chromatographic purification.

It has been shown that adenoviral vectors can successfully be used in eukaryotic gene expression and vaccine development. Recently, animal studies have demonstrated that recombinant adenovirus could be used for gene therapy. Successful studies in administering recombinant adenovirus to different tissues have proven the effectiveness of adenoviral vectors in therapy. This success has led to the use of such vectors in human clinical trials. There now is an increased demand for the production of adenoviral vectors to be used in various therapies. The techniques currently available are insufficient to meet such a demand. The present invention provides methods for the production of large amounts of adenovirus for use in such therapies.

Therefore, the present invention is designed to take advantage of improvements in large scale culturing systems and purification for the purpose of producing and purifying adenoviral vectors. The various components for such a system, and methods of producing adenovirus therewith, are set forth in detail below.

A. Adenovirus

Adenoviruses comprise linear double stranded DNA, with a genome ranging from 30 to 35 kb in size (Reddy et al., 1998; Morrison et al., 1997; Chillon et al., 1999). There are over 50 serotypes of human adenovirus, and over 80 related forms which are divided into six families based on immunological, molecular, and functional criteria (Wadell et al, 1980). Physically, adenovirus is a medium-sized icosahedral virus containing a double-stranded, linear DNA genome which, for adenovirus type 5, is 35,935 base pairs (Chroboczek et al., 1992). Adenoviruses require entry into the host cell and transport of the viral genome to the nucleus for infection of the cell and replication of the virus. Salient features of the adenovirus genome are an early region (E1, E2, E3 and E4 genes), an intermediate region (pIX gene, Iva2 gene), a late region (L1, L2, L3, L4 and L5 genes), a major late promoter (MLP), inverted-terminal-repeats (ITRs) and a ψ sequence (Zheng, et al., 1999; Robbins et al., 1998; Graham and Prevec, 1995). The early genes E1, E2, E3 and E4 are expressed from the virus after infection and encode polypeptides that regulate viral gene expression, cellular gene expression, viral replication, and inhibition of cellular apoptosis. Further on during viral infection, the MLP is activated, resulting in the expression of the late (L) genes, encoding polypeptides required for adenovirus encapsidation. The intermediate region encodes components of the adenoviral capsid. Adenoviral inverted terminal repeats (ITRs; 100-200 bp in length), are cis elements, function as origins of replication and are necessary for viral DNA replication. The ψ sequence is required for the packaging of the adenoviral genome.

The mechanism of infection by adenoviruses, particularly adenovirus serotypes 2 and 5, has been extensively studied. A host cell surface protein designated CAR (Coxsackie Adenoviral Receptor) has been identified as the primary binding receptor for these adenoviruses. The endogenous cellular function of CAR has not yet been elucidated. Interaction between the fiber knob and CAR is sufficient for binding of the adenovirus to the cell surface. However, subsequent interactions between the penton base and additional cell surface proteins, members of the $\alpha_v$, integrin family, are necessary for efficient viral internalization. Disassembly of the adenovirus begins during internalization; the fiber proteins remain on the cell surface bound to CAR. The remainder of the adenovirus is dissembled in a stepwise manner as the viral particle is transported through the cytoplasm to a pore complex at the nuclear membrane. The viral DNA is extruded through the nuclear membrane into the nucleus where viral DNA is replicated, viral proteins are expressed, and new viral particles are assembled. Specific steps in this mechanism of adenoviral infection may be potential targets to modulate viral infection and gene expression.

In certain embodiments of the present invention, the adenovirus used in the methods for producing an adenovirus may be a replication-deficient adenovirus. For example, the adenovirus may be a replication-deficient adenovirus lacking at least a portion of the E1 region. In certain embodiments, the adenovirus may be lacking at least a portion of the E1A and/or E1B region. In other embodiments, the adenovirus is a recombinant adenovirus (discussed further below).

B. Host Cells

Various embodiments of the present invention involve methods for producing an adenovirus. A "host cell" is defined as a cell that is capable of supporting replication of adenovirus. Any cell type for use as a host cell is contemplated by the present invention, as long as the cell is capable of supporting replication of adenovirus. For example, the host cells may be HEK293, PER.C6, 911, or IT293SF cells. One of skill in the art would be familiar with the wide range of host cells that are available for use in methods for producing an adenovirus.

In certain embodiments, the generation and propagation of the adenoviral vectors depend on a unique helper cell line, designated 293, which was transformed from human embryonic kidney cells by Adenovirus serotype 5 (Ad5) DNA fragments and constitutively expresses E1 proteins (Graham et al., 1977). Since the E3 region is dispensable from the Ad genome (Jones and Shenk, 1978), the current Ad vectors, with the help of 293 cells, carry foreign DNA in either the E1, the E3 or both regions (Graham and Prevec, 1991; Bett et al., 1994).

The host cells used in the various embodiments of the present invention may be derived, for example, from mammalian cells such as human embryonic kidney cells or primate c ells. Other cell types might include, but are not limited to Vero cells, CHO cells or any eukaryotic cells for which tissue culture techniques are established as long as the cells are adenovirus permissive. The term "adenovirus permissive" means that the adenovirus or adenoviral vector is able to complete the entire intracellular virus life cycle within the cellular environment.

The host cell may be derived from an existing cell line, e.g., from a 293 cell line, or developed de novo. Such host cells express the adenoviral genes necessary to complement in trans deletions in an adenoviral genome or which supports replication of an otherwise defective adenoviral vector, such as the E1, E2, E4, E5 and late functions. A particular portion of the adenovirus genome, the E1 region, has already been used to generate complementing cell lines. Whether integrated or episomal, portions of the adenovirus genome lacking a viral origin of replication, when introduced into a cell line, will not replicate even when the cell is superinfected with wild-type adenovirus. In addition, because the transcription of the major late unit is after viral DNA replication, the late functions of adenovirus cannot be expressed sufficiently from a cell line. Thus, the E2 regions, which overlap with late functions (L1-5), will be provided by helper viruses and not by the cell line. Typically, a cell line according to the present invention will express E1 and/or E4.

Recombinant host cells, which are host cells that express part of the adenoviral genome, are also contemplated for use as host cells in the present invention. As used herein, the term "recombinant" cell is intended to refer to a cell into which a gene, such as a gene from the adenoviral genome or from another cell, has been introduced. Therefore, recombinant cells are distinguishable from naturally-occurring cells which do not contain a recombinantly-introduced gene. Recombinant cells are thus cells having a gene or genes introduced through "the hand of man."

Recombinant host cells lines are capable of supporting replication of adenovirus recombinant vectors and helper viruses having defects in certain adenoviral genes, i.e., are "permissive" for growth of these viruses and vectors. The recombinant cell also is referred to as a helper cell because of the ability to complement defects in, and support replication of, replication-incompetent adenoviral vectors.

Examples of other useful mammalian cell lines that may be used with a replication competent virus or converted into complementing host cells for use with replication deficient virus are Vero and HeLa cells and cell lines of Chinese hamster ovary, W138, BHK, COS-7, HepG2, 3T3, RN and MDCK cells.

Two methodologies have been used to adapt 293 cells into suspension cultures. Graham adapted 2 93A cells into suspension culture (293N3S cells) by 3 serial passages in nude mice (Graham, 1987). The suspension 293N3S cells were found to be capable of supporting E1 adenoviral vectors. However, Garnier et al. (1994) observed that the 293N35 cells had a relatively long initial lag phase in suspension, a low growth rate, and a strong tendency to clump.

The second method that has been used is a gradual adaptation of 293A cells into suspension growth (Cold Spring Harbor Laboratories, 293S cells). Gamier et al. (1994) reported the use of 293S cells for production of recombinant proteins from adenoviral vectors. The authors found that 293S cells were much less clumpy in calcium-free media and a fresh medium exchange at the time of virus infection could significantly increase the protein production. It was found that glucose was the limiting factor in culture without medium exchange.

1. Growth in Selection Media

In certain embodiments, it may be useful to employ selection systems that preclude growth of undesirable cells. This may be accomplished by virtue of permanently transforming a cell line with a selectable marker or by transducing or infecting a cell line with a viral vector that encodes a selectable marker. In either situation, culture of the transformed/transduced cell with an appropriate drug or selective compound will result in the enhancement, in the cell population, of those cells carrying the marker.

Examples of markers include, but are not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection for dhfr, that confers resistance to methotrexate; gpt, that confers resistance to mycophenolic acid; neo, that confers resistance to the aminoglycoside G418; and hygro, that confers resistance to hygromycin.

2. Growth in Serum Weaning

Serum weaning adaptation of anchorage-dependent cells into serum-free suspension cultures have been used for the production of recombinant proteins (Berg, 1993) and viral vaccines (Perrin, 1995). There have been few reports on the adaptation of 293A cells into serum-free suspension cultures until recently. Gilbert reported the adaptation of 293A cells into serum-free suspension cultures for adenovirus and recombinant protein production (Gilbert, 1996). Similar adaptation method had been used for the adaptation of A 549 cells into serum-free suspension culture for adenovirus production (Morris et al., 1996). Cell-specific virus yields in the adapted suspension cells, however, are about 5-10-fold lower than those achieved in the parental attached cells.

Using the similar serum weaning procedure, the inventors have successfully adapted the 293A cells into serum-free suspension culture (293SF cells). In this procedure, the 293 cells were adapted to a commercially available 293 media by sequentially lowering down the FBS concentration in T-flasks. Briefly, the initial serum concentration in the media was approximately 10% FBS DMEM media in T-75 flask and the cells were adapted to serum-free IS 293 media in T-flasks by lowering down the FBS concentration in the media sequentially. After 6 passages in T-75 flasks the FBS % was estimated to be about 0.019% and the 293 cells. The cells were subcultured two more times in the T flasks before they were transferred to spinner flasks. The results described herein below show that cells grow satisfactorily in the serum-free medium (IS293 medium, Irvine Scientific, Santa Ana, Calif.). Average doubling time of the cells was 20-35 hours achieving stationary cell concentrations in the order of $3-5\times10^6$ cells/ml without medium exchange.

3. Adaptation of Cells for Suspension Culture

Two methodologies have been used to adapt 293 cells into suspension cultures. Graham adapted 293A cells into suspension culture (293N3S cells) by 3 serial passages in nude mice (Graham, 1987). The suspension 293N3S cells were found to be capable of supporting E1 adenoviral vectors. However, Gamier et al. (1994) observed that the 293N35 cells had a relatively long initial lag phase in suspension, a low growth rate, and a strong tendency to clump.

The second method that has been used is a gradual adaptation of 293A cells into suspension growth (Cold Spring Harbor Laboratories, 293S cells). Gamier et al. (1994) reported the use of 293S cells for production of recombinant proteins from adenoviral vectors. The authors found that 293S cells were much less clumpy in calcium-free media and a fresh medium exchange at the time of virus infection could significantly increase the protein production. It was found that glucose was the limiting factor in culture without medium exchange.

In the present invention, the 293 cells adapted for growth in serum-free conditions were adapted into a suspension culture. The cells were transferred in a serum-free 250 mL spinner suspension culture (100 mL working volume) for the suspension culture at an initial cell density of between about 1.18E+5 vc/mL and about 5.22E+5 vc/mL. The media may be supplemented with heparin to prevent aggregation of cells. This cell culture systems allows for some increase of cell density whilst cell viability is maintained. Once these cells are growing in culture, they cells are subcultured in the spinner flasks approximately 7 more passages. It may be noted that the doubling time of the cells is progressively reduced until at the end of the successive passages the doubling time is about 1.3 day, i.e. comparable to 1.2 day of the cells in 10% FBS media in the attached cell culture. In the serum-free IS 293 media supplemented with heparin almost all the cells existed as individual cells not forming aggregates of cells in the suspension culture.

C. Cell Culture Systems

The ability to produce infectious viral vectors is increasingly important to the pharmaceutical industry, especially in the context of gene therapy. Over the last decade, advances in biotechnology have led to the production of a number of important viral vectors that have potential uses as therapies, vaccines and protein production machines. The use of viral vectors in mammalian cultures has advantages over proteins produced in bacterial or other lower life form hosts in their ability to post-translationally process complex protein structures such as disulfide-dependent folding and glycosylation.

Development of cell culture for production of virus vectors has been greatly aided by the development in molecular biology of techniques for design and construction of vector systems highly efficient in mammalian cell cultures, a battery of useful selection markers, gene amplification schemes and a more comprehensive understanding of the biochemical and cellular mechanisms involved in procuring the final biologically-active molecule from the introduced vector.

Frequently, factors which affect the downstream (in this case, beyond the cell lysis) side of manufacturing scale-up were not considered before selecting the cell line as the host for the expression system. Also, development of bioreactor systems capable of sustaining very high density cultures for prolonged periods of time have not lived up to the increasing demand for increased production at lower costs.

The present invention will take advantage of the recently available bioreactor technology. Growing cells according to the present invention in a bioreactor allows for large scale production of fully biologically-active cells capable of being infected by the adenoviral vectors of the present invention. By operating the system at a low perfusion rate and applying a different scheme for purification of the infecting particles, the invention provides a purification strategy that is easily scaleable to produce large quantities of highly purified product.

PCT publication No. WO 98/00524, U.S. Pat. No. 6,194,191, U.S. Published Patent Application No. US-2002-0182723-A1, and U.S. Provisional Patent Application No. 60/406,591 (filed Aug. 28, 2002), which have described viral production methods, are specifically herein incorporated by reference for their description of techniques for culturing, production and purification of recombinant viral particles.

Certain embodiments of the present invention pertain to methods for producing an adenovirus that require the use of a bioreactor. As used herein, a "bioreactor" refers to any apparatus that can be used for the purpose of culturing cells. Growing cells according to the present invention in a bioreactor allows for large scale production of fully biologically-active cells capable of being infected by the adenoviral vectors of the present invention.

Bioreactors have been widely used for the production of biological products from both suspension and anchorage dependent animal cell cultures. The most widely used producer cells for adenoviral vector production are anchorage dependent human embryonic kidney cells (293 cells). Bioreactors to be developed for adenoviral vector production should have the characteristic of high volume-specific culture surface area in order to achieve high producer cell density and high virus yield. Microcarrier cell culture in stirred tank bioreactor provides very high volume-specific culture surface area and has been used for the production of viral vaccines (Griffiths, 1986). Furthermore, stirred tank bioreactors have industrially been proven to be scaleable. The multiplate CELLCUBE™ cell culture system manufactured by Corning-Costar also offers a very high volume-specific culture surface area. Cells grow on both sides of the culture plates hermetically sealed together in the shape of a compact cube. Unlike stirred tank bioreactors, the CELLCUBE™ culture unit is disposable. This is very desirable at the early stage production of clinical product because of the reduced capital expenditure, quality control and quality assurance costs associated with disposable systems. In consideration of the advantages offered by the different systems, both the stirred tank bioreactor and the CELLCUBE™ system were evaluated for the production of adenovirus.

Certain embodiments of the present invention require the use of a WAVE BIOREACTOR®, particularly for use in methods for generating adenovirus in serum-free suspension cultures. The WAVE BIOREACTOR® is a pre-sterilized disposable bioreactor system that can be easily retrofitted with a variety of cleanroom configurations without requiring expensive CIP and SIP process utilities. WAVE BIOREACTOR® can be a WAVE BIOREACTOR® model 20/50EH.

The bioreactor can hold any volume of media, but in a certain embodiment the bioreactor is a 10 L (5 L working volume) bioreactor. In certain embodiments, the bioreactor can be adjusted to rock at a particular speed and angle. In certain other embodiments, the bioreactor may include a device for monitoring dissolved oxygen tension, such as a disposable dissolved oxygen tension (DOT) probe. The bioreactor may also include a device for monitoring temperature in the media. Other embodiments include a device for measuring and adjusting culture pH, such as a gas mixer which can adjust $CO_2$ gas percentage delivered to the media. The bioreactor may or may not be a disposable bioreactor. According to a preferred aspect of the invention, the WAVE BIOREACTOR® is used with serum-free media and the initial lactate concentration of the medium is made as low as possible because high lactate concentration inhibits virus production. Further, an adequate glucose concentration should be maintained as glucose limitation can also inhibit virus production. As used herein, "media" and "medium" refers to any substance which can facilitate growth of cells. According to one aspect of the present invention, the host cells are grown in media that is serum-free media. In other embodiments of the present invention, the host cells are grown in media that is protein-free media. One example of a protein-free media is CD293. Another example of media that can support host cell growth in a particular embodiment of the invention is DMEM+2% FBS. On of skill in the art would understand that various components and agents can be added to the media to facilitate and control cell growth. For example, the glucose concentration of the media can be maintained at a certain level. In one embodiment of the present methods for producing adenovirus, the glucose concentration is maintained between about 0.5 and about 3.0 gm glucose/liter.

1. Anchorage-Dependent Versus Non-Anchorage-Dependent Cultures

In some embodiments of the present invention, the methods for producing an adenovirus require growing host cells in anchorage-dependent cultures, whereas other embodiments pertain to methods for producing an adenovirus in non-anchorage-dependent cultures. Animal and human cells can be propagated in vitro in two modes: as non-anchorage dependent cells growing freely in suspension throughout the bulk of the culture; or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. Large scale suspension culture based on microbial (bacterial and yeast) fermentation technology has clear advantages for the manufacturing of mammalian cell products. The processes are relatively simple to operate and straightforward to scale up. Homogeneous conditions can be provided in the reactor which allows for precise monitoring and control of temperature, dissolved oxygen, and pH, and ensure that representative samples of the culture can be taken.

However, suspension cultured cells cannot always be used in the production of biologicals. Suspension cultures are still considered to have tumorigenic potential and thus their use as substrates for production put limits on the use of the resulting products in human and veterinary applications (Petricciani, 1985; Larsson, 1987). Viruses propagated in suspension cultures as opposed to anchorage-dependent cultures can sometimes cause rapid changes in viral markers, leading to reduced immunogenicity (Bahnemann, 1980). Finally, sometimes even recombinant cell lines can secrete considerably higher amounts of products when propagated as anchorage-dependent cultures as compared with the same cell line in suspension (Nilsson and Mosbach, 1987). For these reasons, different types of anchorage-dependent cells are used extensively in the production of different biological products.

2. Reactors and Processes for Suspension

The bioreactors utilized in the context of selected embodiments of the present invention may be stirred tank bioreactors. Large scale suspension culture of mammalian cultures in stirred tanks have been described. The instrumentation and controls for bioreactors adapted, along with the design of the fermentors, from related microbial applications. However, acknowledging the increased demand for contamination control in the slower growing mammalian cultures, improved aseptic designs were quickly implemented, improving dependability of these reactors. Instrumentation and controls are basically the same as found in other fermentors and include agitation, temperature, dissolved oxygen, and pH controls. More advanced probes and autoanalyzers for on-line and off-line measurements of turbidity (a function of particles present), capacitance (a function of viable cells present), glucose/lactate, carbonate/bicarbonate and carbon dioxide are available. In one embodiment of the present invention, the autoanalyzer is a YSI-2700 SELECT™ analyzer.

Two suspension culture reactor designs are most widely used in the industry due to their simplicity and robustness of operation—the stirred reactor and the airlift reactor. The stirred reactor design has successfully been used on a scale of 8000 liter capacity for the production of interferon (Phillips et al., 1985; Mizrahi, 1983). Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor, and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gasses and generates relatively low shear forces.

Most large-scale suspension cultures are operated as batch or fed-batch processes because they are the most straightforward to operate and scale up. However, continuous processes based on chemostat or perfusion principles are available.

A batch process is a closed system in which a typical growth profile is seen. A lag phase is followed by exponential, stationary and decline phases. In such a system, the environment is continuously changing as nutrients are depleted and metabolites accumulate. This makes analysis of factors influencing cell growth and productivity, and hence optimization of the process, a complex task. Productivity of a batch process may be increased by controlled feeding of key nutrients to prolong the growth cycle. Such a fed-batch process is still a closed system because cells, products and waste products are not removed.

In what is still a closed system, perfusion of fresh medium through the culture can be achieved by retaining the cells with a variety of devices (e.g. fine mesh spin filter, hollow fiber or flat plate membrane filters, settling tubes). Spin filter cultures can produce cell densities of approximately $5 \times 10^7$ cells/ml. A true open system and the simplest perfusion process is the chemostat in which there is an inflow of medium and an outflow of cells and products. Culture medium is fed to the reactor at a predetermined and constant rate which maintains the dilution rate of the culture at a value less than the maximum specific growth rate of the cells (to prevent washout of the cell mass from the reactor). Culture fluid containing cells and cell products and byproducts is removed at the same rate.

In certain embodiments of the present methods for producing adenovirus, the bioreactor system is set up to include a system to allow for media exchange. For example, filters may be incorporated into the bioreactor system to allow for separation of cells from spent media to facilitate media exchange. In some embodiments of the present methods for producing adenovirus, media exchange and perfusion is conducted beginning on a certain day of cell growth. For example, media exchange and perfusion can begin on day 3 of cell growth. The filter may be external to the bioreactor, or internal to the bioreactor.

In one embodiment of the present invention, the filter is a floating flat filter that is internal to the bioreactor. The filter provides for separation between the cells and spent medium. In certain embodiments, the spent culture media is withdrawn through the floating filer. Recirculation of the media may or may not be required in the various embodiments of the present invention. In one embodiment, wave action is used to minimize clogging of the filter during media perfusion. The culture volume may be maintained by a load cell used to trigger fresh medium addition. One of skill in the art would be familiar with the various types of filters that can be used for perfusion of media, and the various methods that can be employed for attaching the filter to the bioreactor and incorporating it into the cell growth process.

3. Non-Perfused Attachment Systems

Traditionally, anchorage-dependent cell cultures are propagated on the bottom of small glass or plastic vessels. The restricted surface-to-volume ratio offered by classical and traditional techniques, suitable for the laboratory scale, has created a bottleneck in the production of cells and cell products on a large scale. In an attempt to provide systems that offer large accessible surfaces for cell growth in small culture volume, a number of techniques have been proposed: the roller bottle system, the stack plate's propagator, the spiral film bottles, the hollow fiber system, the packed bed, the plate exchanger system, and the membrane tubing reel. Since these systems are non-homogeneous in their nature, and are sometimes based on multiple processes, they suffer from the following shortcomings—limited potential for scale-up, difficulties in taking cell samples, limited potential for measuring and controlling key process parameters and difficulty in maintaining homogeneous environmental conditions throughout the culture.

Despite these drawbacks, a commonly used process for large scale anchorage-dependent cell production is the roller bottle. Being little more than a large, differently shaped T-flask, simplicity of the system makes it very dependable and, hence, attractive. Fully automated robots are available that can handle thousands of roller bottles per day, thus eliminating the risk of contamination and inconsistency associated with the otherwise required intense human handling. With frequent media changes, roller bottle cultures can achieve cell densities of close to $0.5 \times 10^6$ cells/cm$^2$ (corresponding to approximately $10^9$ cells/bottle or almost $10^7$ cells/ml of culture media).

4. Cultures on Microcarriers

In an effort to overcome the shortcomings of the traditional anchorage-dependent culture processes, van Wezel (1967) developed the concept of the microcarrier culturing systems. In this system, cells are propagated on the surface of small solid particles suspended in the growth medium by slow agitation. Cells attach to the microcarriers and grow gradually to confluency on the microcarrier surface. In fact, this large scale culture system upgrades the attachment dependent culture from a single disc process to a unit process in which both monolayer and suspension culture have been brought together. Thus, combining the necessary surface for a cell to grow with the advantages of the homogeneous suspension culture increases production.

The advantages of microcarrier cultures over most other anchorage-dependent, large-scale cultivation methods are several fold. First, microcarrier cultures offer a high surface-to-volume ratio (variable by changing the carrier concentration) which leads to high cell density yields and a potential for obtaining highly concentrated cell products. Cell yields are up to $1-2 \times 10^7$ cells/ml when cultures are propagated in a perfused reactor mode. Second, cells can be propagated in one unit process vessels instead of using many small low-productivity vessels (i.e., flasks or dishes). This results in far better nutrient utilization and a considerable saving of culture medium. Moreover, propagation in a single reactor leads to reduction in need for facility space and in the number of handling steps required per cell, thus reducing labor cost and risk of contamination. Third, the well-mixed and homogeneous microcarrier suspension culture makes it possible to monitor and control environmental conditions (e.g., pH, pO$_2$, and concentration of medium components), thus leading to more reproducible cell propagation and product recovery. Fourth, it is possible to take a representative sample for microscopic observation, chemical testing, or enumeration. Fifth, since microcarriers settle out of suspension quickly, use of a fed-batch process or harvesting of cells can be done relatively easily. Sixth, the mode of the anchorage-dependent culture propagation on the microcarriers makes it possible to use this system for other cellular manipulations, such as cell transfer without the use of proteolytic enzymes, cocultivation of cells, transplantation into animals, and perfusion of the culture using decanters, columns, fluidized beds, or hollow fibers for microcarrier retainment. Seventh, microcarrier cultures are relatively easily scaled up using conventional equipment used for cultivation of microbial and animal cells in suspension.

5. Microencapsulation of Mammalian Cells

One method which has shown to be particularly useful for culturing mammalian cells is microencapsulation. The mammalian cells are retained inside a semipermeable hydrogel membrane. A porous membrane is formed around the cells permitting the exchange of nutrients, gases, and metabolic products with the bulk medium surrounding the capsule. Several methods have been developed that are gentle, rapid and non-toxic and where the resulting membrane is sufficiently porous and strong to sustain the growing cell mass throughout the term of the culture. These methods are all based on soluble alginate gelled by droplet contact with a calcium-containing solution. Lim (1982, U.S. Pat. No. 4,352,883, incorporated herein by reference,) describes cells concentrated in an approximately 1% solution of sodium alginate which are forced through a small orifice, forming droplets, and breaking free into an approximately 1% calcium chloride solution. The droplets are then cast in a layer of polyamino acid that ionically bonds to the surface alginate. Finally the alginate is reliquefied by treating the droplet in a chelating agent to remove the calcium ions. Other methods use cells in a calcium solution to be dropped into a alginate solution, thus creating a hollow alginate sphere. A similar approach involves cells in a chitosan solution dropped into alginate, also creating hollow spheres.

Microencapsulated cells are easily propagated in stirred tank reactors and, with beads sizes in the range of 150-1500 .mu.m in diameter, are easily retained in a perfused reactor using a fine-meshed screen. The ratio of capsule volume to total media volume can be maintained from as dense as 1:2 to 1:10. With intracapsular cell densities of up to $10^8$, the effective cell density in the culture is $1-5 \times 10^7$.

The advantages of microencapsulation over other processes include the protection from the deleterious effects of shear stresses which occur from sparging and agitation, the ability to easily retain beads for the purpose of using perfused systems, scale up is relatively straightforward and the ability to use the beads for implantation. The current invention includes cells which are anchorage-dependent in nature. 293 cells, for example, are anchorage-dependent, and when grown in suspension, the cells will attach to each other and grow in clumps, eventually suffocating cells in the inner core of each clump as they reach a size that leaves the core cells unsustainable by the culture conditions. Therefore, an efficient means of large-scale culture of anchorage-dependent cells is needed in order to effectively employ these cells to generate large quantities of adenovirus.

6. Perfused Attachment Systems

Certain embodiments of the present invention involve methods for producing an adenovirus that involve use of perfused attachment systems. Perfusion refers to continuous flow at a steady rate, through or over a population of cells (of a physiological nutrient solution). It implies the retention of the cells within the culture unit as opposed to continuous-flow culture which washes the cells out with the withdrawn media (e.g., chemostat). The idea of perfusion has been known since the beginning of the century, and has been applied to keep small pieces of tissue viable for extended microscopic observation. The technique was initiated to mimic the cells milieu in vivo where cells are continuously supplied with blood, lymph, or other body fluids. Without perfusion, cells in culture go through alternating phases of being fed and starved, thus limiting full expression of their growth and metabolic potential.

The current use of perfused culture is in response to the challenge of growing cells at high densities (i.e., $0.1-5 \times 10^8$ cells/ml). In order to increase densities beyond $2-4 \times 10^6$ cells/ml, the medium has to be constantly replaced with a fresh supply in order to make up for nutritional deficiencies and to remove toxic products. Perfusion allows for a far better control of the culture environment (pH, $pO_2$, nutrient levels, etc.) and is a means of significantly increasing the utilization of the surface area within a culture for cell attachment.

The development of a perfused packed-bed reactor using a bed matrix of a non-woven fabric has provided a means for maintaining a perfusion culture at densities exceeding $10^8$ cells/ml of the bed volume (CelliGen™, New Brunswick Scientific, Edison, N.J.; Wang et al., 1992; Wang et al., 1993; Wang et al., 1994). Briefly described, this reactor comprises an improved reactor for culturing of both anchorage- and non-anchorage-dependent cells. The reactor is designed as a packed bed with a means to provide internal recirculation. Preferably, a fiber matrix carrier is placed in a basket within the reactor vessel. A top and bottom portion of the basket has holes, allowing the medium to flow through the basket. A specially designed impeller provides recirculation of the medium through the space occupied by the fiber matrix for assuring a uniform supply of nutrient and the removal of wastes. This simultaneously assures that a negligible amount of the total cell mass is suspended in the medium. The combination of the basket and the recirculation also provides a bubble-free flow of oxygenated medium through the fiber matrix. The fiber matrix is a non-woven fabric having a "pore" diameter of from 10 .mu.m to 100 .mu.m, providing for a high internal volume with pore volumes corresponding to 1 to 20 times the volumes of individual cells.

In comparison to other culturing systems, this approach offers several significant advantages. With a fiber matrix carrier, the cells are protected against mechanical stress from agitation and foaming. The free medium flow through the basket provides the cells with optimum regulated levels of oxygen, pH, and nutrients. Products can be continuously removed from the culture and the harvested products are free of cells and can be produced in low-protein medium which facilitates subsequent purification steps. Also, the unique design of this reactor system offers an easier way to scale up the reactor. Currently, sizes up to 30 liter are available. One hundred liter and 300 liter versions are in development and theoretical calculations support up to a 1000 liter reactor. This technology is explained in detail in WO 94/17178 (Aug. 4, 1994, Freedman et al.), which is hereby incorporated by reference in its entirety.

The Cellcube™ (Corning-Costar) module provides a large styrenic surface area for the immobilization and growth of substrate attached cells. It is an integrally encapsulated sterile single-use device that has a series of parallel culture plate joined to create thin sealed laminar flow spaces between adjacent plates.

The Cellcube module has inlet and outlet ports that are diagonally opposite each other and help regulate the flow of media. During the first few days of growth the culture is generally satisfied by the media contained within the system after initial seeding. The amount of time between the initial seeding and the start of the media perfusion is dependent on the density of cells in the seeding inoculum and the cell growth rate. The measurement of nutrient concentration in the circulating media is a good indicator of the status of the culture. When establishing a procedure it may be necessary to monitor the nutrients composition at a variety of different perfusion rates to determine the most economical and productive operating parameters.

Cells within the system reach a higher density of solution (cells/n-11) than in traditional culture systems. Many typically used basal media are designed to support $1-2 \times 106$ cells/ml/day. A typical CELLCUBE™ run with an 85,000 $cm^2$ surface, contains approximately 6 L media within the module. The cell density often exceeds $10^7$ cells/mL in the culture vessel. At confluence, 2-4 reactor volumes of media are required per day.

The timing and parameters of the production phase of cultures depends on the type and use of a particular cell line. Many cultures require a different media for production than is required for the growth phase of the culture. The transition from one phase to the other will likely require multiple washing steps in traditional cultures. However, the CELLCUBE™ system employs a perfusion system. On of the benefits of such a system is the ability to provide a gentle transition between various operating phases. The perfusion system negates the need for traditional wash steps that seek to remove serum components in a growth medium.

7. Serum-Free Suspension Culture

In particular embodiments, adenoviral vectors for gene therapy are produced from anchorage-dependent culture of 293 cells (293A cells) as described above. Scale-up of adenoviral vector production is constrained by the anchorage-dependency of 293A cells. To facilitate scale-up and meet future demand for adenoviral vectors, significant efforts have been devoted to the development of alternative production processes that are amenable to scale-up. Methods include growing 293A cells in microcarrier cultures and adaptation of 293A producer cells into suspension cultures.

Microcarrier culture techniques have been described above. This technique relies on the attachment of producer cells onto the surfaces of microcarriers which are suspended in culture media by mechanical agitation. The requirement of cell attachment may present some limitations to the scaleability of microcarrier cultures. In certain embodiments of the present invention, the media used in the methods for producing an adenovirus is a serum-free media. In other embodiments of the present invention, the media is a protein-free media. As previously discussed, certain embodiments of the present invention involve use of bioreactors. The bioreactors may be adapted for serum-free suspension culture of cells. Filtration of media with media exchange may or may not be included in the system.

D. Viral Infection

The present invention pertains to methods of producing an adenovirus that include infecting the host cells with an adenovirus. Typically, the virus will simply be exposed to the appropriate host cell under physiologic conditions, permitting uptake of the virus. One of skill in the art would be familiar with the wide range of techniques available for initiating virus infection.

The present invention employs, in one example, adenoviral infection of cells in order to generate therapeutically significant vectors. Typically, the virus will simply be exposed to the appropriate host cell under physiologic conditions, permitting uptake of the virus. Though adenovirus is exemplified, the present methods may be advantageously employed with other viral vectors, as discussed below.

1. Adenovirus

Adenovirus is particularly suitable for use as a gene transfer vector because of its mid-sized DNA genome, ease of manipulation, high titer, wide target-cell range, and high infectivity. The roughly 36 kB viral genome is bounded by 100-200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products. Elimination of large potions of the adenoviral genome, and providing the delete gene products in trans, by helper virus and/or helper cells, allows for the insertion of large portions of heterologous DNA into the vector. This strategy also will result in reduced toxicity and immunogenicity of the adenovirus gene products.

The large displacement of DNA is possible because the cis elements required for viral DNA replication all are localized in the inverted terminal repeats (ITR) (100-200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194-385 bp (0.5-1.1 map units) at the left end of the viral genome (Hearing et al., 1987). This signal mimics the protein recognition site in bacteriophage .lambda. DNA where a specific sequence close to the left end, but outside the cohesive end sequence, mediates the binding to proteins that are required for insertion of the DNA into the head structure. E1 substitution vectors of Ad have demonstrated that a 450 bp (0-1.25 map units) fragment at the left end of the viral genome could direct packaging in 293 cells (Levrero et al., 1991).

Previously, it has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

Replication-deficient adenoviral vectors can be complemented, in trans, by helper virus. This observation alone does not permit isolation of the replication-deficient vectors, however, since the presence of helper virus, needed to provide replicative functions, would contaminate any preparation. Thus, an additional element was needed that would add specificity to the replication and/or packaging of the replication-deficient vector. That element, as provided for in the present invention, derives from the packaging function of adenovirus.

It has been shown that a packaging signal for adenovirus exists in the left end of the conventional adenovirus map (Tibbetts, 1977). Later studies showed that a mutant with a deletion in the E1A (194-358 bp) region of the genome grew poorly even in a cell line that complemented the early (E1A) function (Hearing and Shenk, 1983). When a compensating adenoviral DNA (0-353 bp) was recombined into the right end of the mutant, the virus was packaged normally. Further mutational analysis identified a short, repeated, position-dependent element in the left end of the Ad5 genome. One copy of the repeat was found to be sufficient for efficient packaging if present at either end of the genome, but not when moved towards the interior of the Ad5 DNA molecule (Hearing et al., 1987).

By using mutated versions of the packaging signal, it is possible to create helper viruses that are packaged with varying efficiencies. Typically, the mutations are point mutations or deletions. When helper viruses with low efficiency packaging are grown in helper cells, the virus is packaged, albeit at reduced rates compared to wild-type virus, thereby permitting propagation of the helper. When these helper viruses are grown in cells along with virus that contains wild-type packaging signals, however, the wild-type packaging signals are recognized preferentially over the mutated versions. Given a limiting amount of packaging factor, the virus containing the wild-type signals are packaged selectively when compared to the helpers. If the preference is great enough, stocks approaching homogeneity should be achieved.

2. Retrovirus

Although adenoviral infection of cells for the generation of therapeutically significant vectors is a preferred embodiments of the present invention, it is contemplated that the present invention may employ retroviral infection of cells for the purposes of generating such vectors. The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes—gag, pol and env—that code for capsid proteins, polymerase enzyme, and envelope components, respectively. A sequence found upstream from the gag gene, termed Y, functions as a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a promoter is inserted into the viral genome in the place of certain viral sequences to produce a virus that is replication-defective. In order to produce virions, a packaging cell line containing the gag, pol and env genes but without the LTR and Y components is constructed (Mann et al., 1983). When a recombinant plasmid containing a human cDNA, together with the retroviral LTR and Y sequences is introduced into this cell line (by calcium phosphate precipitation for example), the Y sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of galactose residues to the viral envelope. This modification could permit the specific infection of cells such as hepatocytes via asialoglycoprotein receptors, should this be desired.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, the infection of a variety of human cells that bore those surface antigens was demonstrated with an ecotropic virus in vitro (Roux et al., 1989).

3. Other Viral Vectors

Other viral vectors may be employed as expression constructs in the present invention. Vectors derived from viruses such as vaccinia virus (Ridgeway, 1988; Baichwal and Sugden, 1986; Coupar et al., 1988), adeno-associated virus (AAV) (Ridgeway, 1988; Baichwal and Sugden, 1986; Hermonat and Muzycska, 1984), herpes viruses and lentivirus may be employed. These viruses offer several features for use in gene transfer into various mammalian cells.

4. Methods of Gene Transfer

In order to create the helper cell lines of the present invention, and to create recombinant adenovirus vectors for use therewith, various genetic (i.e. DNA) constructs must be delivered to a cell. One way to achieve this is via viral transductions using infectious viral particles, for example, by transformation with an adenovirus vector of the present invention. Alternatively, retroviral or bovine papilloma virus may be employed, both of which permit permanent transformation of a host cell with a gene(s) of interest. In other situations, the nucleic acid to be transferred is not infectious, i.e., contained in an infectious virus particle. This genetic material must rely on non-viral methods for transfer.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979), cell sonication (Fechheimer et al., 1987), gene bombardment using high velocity microprojectiles (Yang et al., 1990), and receptor-mediated transfection (Wu, 1987; Wu and Wu, 1988).

Once the construct has been delivered into the cell the nucleic acid encoding the therapeutic gene may be positioned and expressed at different sites. In certain embodiments, the nucleic acid encoding the therapeutic gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In one embodiment of the invention, the expression construct may simply consist of naked recombinant DNA or plasmids. Transfer of the construct may be performed by any of the methods mentioned above which physically or chemically permeabilize the cell membrane. This is particularity applicable for transfer in vitro, however, it may be applied for in vivo use as well. Dubensky et al. (1984) successfully injected polyomavirus DNA in the form of CaPO4 precipitates into liver and spleen of adult and newborn mice demonstrating active viral replication and acute infection. Benvenisty and Neshif (1986) also demonstrated that direct intraperitoneal injection of CaPO4 precipitated plasmids results in expression of the transfected genes. It is envisioned that DNA encoding a CAM may also be transferred in a similar manner in vivo and express CAM.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

In a further embodiment of the invention, the expression construct may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Liposome-mediated nucleic acid delivery and expression of foreign DNA in vitro has been very successful. Using the .beta.-lactamase gene, Wong et al. (1980) demonstrated the feasibility of liposome-mediated delivery and expression of foreign DNA in cultured chick embryo, HeLa, and hepatoma cells. Nicolau et al. (1987) accomplished successful liposome-mediated gene transfer in rats after intravenous injection. Also included are various commercial approaches involving "lipofection" technology.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear nonhistone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention.

Other expression constructs which can be employed to deliver a nucleic acid encoding a therapeutic gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferring (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (1987) employed lactosyl-ceramide, a galactose-terminal asialgan-glioside, incorporated into liposomes and observed an increase in the uptake of the insulin gene by hepatocytes. Thus, it is feasible that a nucleic acid encoding a therapeutic gene also may be specifically delivered into a cell type such as prostate, epithelial or tumor cells, by any number of receptor-ligand systems with or without liposomes. For example, the human prostate-specific antigen (Watt et al., 1986) may be used as the receptor for mediated delivery of a nucleic acid in prostate tissue.

In certain embodiments of the present invention, the temperature at which infection of the host cells is performed is 37° C. However, in other embodiments, the infection temperature is at temperature that is less than 37° C. This is based on the inventors' discovery that infection temperatures less than 37° C. provide for optimal production of adenovirus. Thus, for example, the temperature may be 32.1° C., 32.2° C., 32.3° C., 32.4° C., 32.5° C., 32.6° C., 32.7° C., 32.8° C., 32.9° C., 33.0° C., 33.1° C., 33.2, 33.3° C., 33.4° C., 33.5° C., 33.6° C., 33.7° C., 33.8° C., 33.0° C., 34.0° C., 34.1° C., 34.2° C., 334.3° C., 35.5° C., 35.6° C., 35.7° C., 35.8° C., 35.9° C., 36.0° C., 36.1° C., 36.2° C., 36.3° C., 36.4° C., 36.5° C., 36.6° C., 36.7° C., 36.8° C., and 36.9° C. temperature or increments of temperature derivable therein. Any method known to those of skill in the art may be used to measure the temperature of the cell culture media. One of skill in the art would be familiar with the wide range of methods available for measuring the temperature of culture media.

For example, one convenient way to measure temperature would be to use a real time digital device to measure the temperature inside an incubator. Prior to the procedure, the digital device can be calibrated using traceable temperature calibration equipment to verify accuracy of the digital device.

In certain embodiments of the present invention, the methods for producing an adenovirus may involve initiating virus infection by diluting the host cells with fresh media and adenovirus. This avoids the need for a separate medium exchange step prior to infection. The invention contemplates that any amount of dilution of the host cells is contemplated by the present invention. The invention also contemplates any amount of virus added to initiate infection. However, in a certain embodiment of the present invention, virus infection will be initiated by adding 50 vp/host cell.

The embodiments of the present invention contemplate that virus infection can be allowed to proceed for any length of time. However, in a certain embodiment, virus infection is allowed to proceed for 4 days. In another embodiment of the present invention, host cell growth is allowed to occur in one bioreactor, and infection of host cells is conducted in a second bioreactor.

The term "adenovirus preparation" will be used herein to describe the reaction mixture following initiation of infection with adenovirus. The adenovirus preparation may include host cells that have undergone lysis, cell fragments, adenovirus, media, and any other components present in the reaction mixture during infection. The adenovirus preparation may include intact host cells, depending on how long infection was allowed to proceed. Some or all of the host cells may have undergone cell lysis, with release of viral particles into the surrounding media. The present invention contemplates that in the embodiments of the methods for producing an adenovirus, adenovirus isolation will occur at any time and by any means known to those of skill in the art following infection. For example, in one embodiment of the present invention, isolating the adenovirus from the adenovirus preparation occurs 4 days after viral infection is completed.

E. Engineering of Viral Vectors

1 Viral Vectors

In particular embodiments, a recombinant adenovirus is contemplated for the delivery of expression constructs. "Recombinant adenovirus," "adenovirus vector" or "adenoviral expression vector" is meant to include those constructs containing adenovirus sequences sufficient to (a) support packaging of the construct and (b) to ultimately express a tissue or cell-specific construct that has been cloned therein. The recombinant adenovirus may encode a recombinant gene. Thus, a recombinant adenovirus may include any of the engineered vectors that comprise adenoviral sequences.

An adenovirus expression vector according to the present invention comprises a genetically engineered form of the adenovirus. The nature of the adenovirus vector is not believed to be crucial to the successful practice of the invention. The adenovirus may be of any of the known serotypes and/or subgroups A-F. Adenovirus type 5 of subgroup C is the preferred starting material in order to obtain one adenovirus vector for use in the present invention. This is because adenovirus type 5 is a human adenovirus about which a great deal of biochemical and genetic information is known, and it has historically been used for most constructions employing adenovirus as a vector.

Advantages of adenoviral gene transfer include the ability to infect a wide variety of cell types, including non-dividing cells, a mid-sized genome, ease of manipulation, high infectivity and they can be grown to high titers (Wilson, 1996). Further, adenoviral infection of host cells does not result in chromosomal integration because adenoviral DNA can replicate in an episomal manner, without potential genotoxicity associated with other viral vectors. Adenoviruses also are structurally stable (Marienfeld et al., 1999) and no genome rearrangement has been detected after extensive amplification (Parks et al., 1997; Bett et al., 1993).

Adenovirus growth and manipulation is known to those of skill in the art, and exhibits broad host range in vitro and in vivo (U.S. Pat. No. 5,670,488; U.S. Pat. No. 5,932,210; U.S. Pat. No. 5,824,544). This group of viruses can be obtained in high titers, e.g., $10^9$ to $10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells.

Although adenovirus based vectors offer several unique advantages over other vector systems, they often are limited by vector immunogenicity, size constraints for insertion of recombinant genes, low levels of replication, and low levels of transgene expression. A major concern in using adenoviral vectors is the generation of a replication-competent virus during vector production in a packaging cell line or during gene therapy treatment of an individual. The generation of a replication-competent virus could pose serious threat of an unintended viral infection and pathological consequences for the patient.

Certain embodiments of the present invention pertain to methods of producing an adenovirus that involve replication-deficient adenovirus. Armentano et al., describe the preparation of a replication-deficient adenovirus vector, claimed to eliminate the potential for the inadvertent generation of a replication-competent adenovirus (U.S. Pat. No. 5,824,544). The replication-deficient adenovirus method comprises a deleted E1 region and a relocated protein IX gene, wherein the vector expresses a heterologous, mammalian gene.

A common approach for generating a denoviruses for use as a gene transfer vector is the deletion of the E1 gene (E1), which is involved in the induction of the E2, E3 and E4 promoters (Graham and Prevec, 1995). Subsequently, a therapeutic gene or genes can be inserted recombinantly in place of the E1 gene, wherein expression of the therapeutic gene(s) is driven by the E1 promoter or a heterologous promoter. The E1", replication-deficient virus is then proliferated in a "helper" cell line that provides the E1 polypeptides in trans (e.g., the human embryonic kidney cell line 293). Alternatively, the E3 region, portions of the E4 region or both may be deleted, wherein a heterologous nucleic acid sequence under the control of a promoter operable in eukaryotic cells is inserted into the adenovirus genome for use in gene transfer (U.S. Pat. No. 5,670,488; U.S. Pat. No. 5,932,210).

2. Viral Vectors Encoding Therapeutic Genes

In certain embodiments, the invention may include methods of producing an adenovirus where the adenovirus is a recombinant adenovirus encoding a recombinant gene. The recombinant gene may be operatively linked to a promoter. In certain other embodiments, the recombinant gene is a therapeutic gene. The invention contemplates use of any gene that has therapeutic or potential therapeutic value in the treatment of a disease or genetic disorder. One of skill in the art would be familiar with the wide range of such genes that have been identified.

Gene therapy generally involves the introduction into cells of therapeutic genes, also known as transgenes, whose expression results in amelioration or treatment of disease or genetic disorders. The therapeutic genes involved may be those that encode proteins, structural or enzymatic RNAs, inhibitory products such as antisense RNA or DNA, or any other gene product. Expression is the generation of such a gene product or the resultant effects of the generation of such a gene product. Thus, enhanced expression includes the greater production of any therapeutic gene or the augmentation of that product's role in determining the condition of the cell, tissue, organ or organism. The delivery of therapeutic genes by adenoviral vectors involves what may be termed transduction of cells. As used here, transduction is defined as the introduction into a cell a therapeutic gene, transgene, or transgene construct by an adenoviral or related vector.

Many experiments, innovations, preclinical studies and clinical trials are currently under investigation for the use of adenoviruses as gene delivery vectors. For example, adenoviral gene delivery-based gene therapies are being developed for liver diseases (Han et al., 1999), psychiatric diseases (Lesch, 1999), neurological diseases (Hermens and Verhaagen, 1998), coronary diseases (Feldman et al., 1996), muscular diseases (Petrof, 1998), and various cancers such as colorectal (Dorai et al., 1999), bladder (Irie et al., 1999), prostate (Mincheff et al., 2000), head and neck (Blackwell et al., 1999), breast (Stewart et al., 1999), lung (Batra et al., 1999) and ovarian (Vanderkwaak et al., 1999).

The particular therapeutic gene encoded by the adenoviral vector is not limiting and includes those useful for various therapeutic and research purposes, as well as reporter genes and reporter gene systems and constructs useful in tracking the expression of transgenes and the effectiveness of adenoviral and adenoviral vector transduction. Thus, by way of example, the following are classes of possible genes whose expression may be enhanced by using the compositions and methods of the present invention: developmental genes (e.g. adhesion molecules, cyclin kinase inhibitors, Wnt family members, Pax family members, Winged helix family members, Hox family members, cytokines/lymphokines and their receptors, growth or differentiation factors and their receptors, neurotransmitters and their receptors), oncogenes (e.g. ABLI, BLC1, BCL6, CBFA1, CBL, CSFIR, ERBA, ERBB, EBRB2, ETS1, ETS1, ETV6, FGR, FOX, FYN, HCR, BRAS, JUN, KRAS, LCK, LYN, MDM2, MLL, MYB, MYC, MYCL1, MYCN, NRAS, PIM1, PML, RET, SRC, TAL1, TCL3 and YES), tumor suppresser genes (e.g. APC, BRCA1, BRCA2, MADH4, MCC, NF1, NF2, RB1, TP53 and WT1), enzymes (e.g. ACP desaturases and hycroxylases, ADP-glucose pyrophorylases, ATPases, alcohol dehycrogenases, amylases, amyloglucosidases, catalases, cellulases, cyclooxygenases, decarboxylases, dextrinases, esterases, DNA and RNA polymerases, hyaluron synthases, galactosidases, glucanases, glucose oxidases, GTPases, helicases, hemicellulases, hyaluronidases, integrases, invertases, isomersases, kinases, lactases, lipases, lipoxygenases, lyases, lysozymes, pectinesterases, peroxidases, phosphatases, phospholipases, phophorylases, polygalacturonases, proteinases and peptideases, pullanases, recombinases, reverse transcriptases, topoisomerases, iylanases), reporter genes (e.g. Green fluorescent protein and its many color variants, luciferase, CAT reporter systems, Beta-galactosidase, etc.), blood derivatives, hormones, lymphokines (including interleuldns), interferons, TNF, growth factors, neurotransmitters or their precursors or synthetic enzymes, trophic factors (such as BDNF, CNTF, NGF, GMF, aFGF, bFGF, NT3, NT5, and the like), apolipoproteins (such as ApoAI, ApoAIV, ApoE, and the like), dystrophin or a minidystrophic, tumor suppressor genes (such as p53, Rb, Rap 1 A, DCC, k-rev, and the like), genes coding for factors involved in coagulation (such as factors VII, VIII, IX, and the like), suicide genes (such as thymidine kinase), cytosine deaminase, or all or part of a natural or artificial immunoglobulin (Fab, ScFv, and the like). Other examples of therapeutic genes include fus, interferon α, interferon β, interferon γ, ADP (adenoviral death protein).

The therapeutic gene can also be an antisense gene or sequence whose expression in the target cell enables the expression of cellular genes or the transcription of cellular mRNA to be controlled, or instance ribozymes. Such sequence can, for example, be transcribed in the target cell into RNAs complementary to cellular mRNAs. The therapeutic gene can also be a gene coding for an antigenic peptide capable of generating an immune response in man. In this particular embodiment, the invention hence makes it possible to produce vaccines enabling humans to be immunized, in particular against microorganisms and viruses.

The tumor suppressor oncogenes function to inhibit excessive cellular proliferation. The inactivation of these genes destroys their inhibitory activity, resulting in unregulated proliferation. The tumor suppressors p53, p16 and C-CAM are described below.

p53 currently is recognized as a tumor suppressor gene. High levels of mutant p53 have been found in many cells transformed by chemical carcinogenesis, ultraviolet radiation, and several viruses, including SV40. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

The p53 gene encodes a 393-amino-acid phophoprotein that can form complexes with host proteins such as large-T antigen and .E1B. The protein is found in normal tissues and cells, but at concentrations which are minute by comparison with transformed cells or tumor tissue. Interestingly, wild-type p53 appears to be important in regulating cell growth and division. Overexpression of wild-type p53 has been shown in some cases to be anti-proliferative in human tumor cell lines. Thus, p53 can act as a negative regulator of cell growth (Weinberg, 1991) and may directly suppress uncontrolled cell growth or indirectly activate genes that suppress this growth. Thus, absence or inactivation of wild-type p53 may contribute to transformation. However, some studies indicate that the presence of mutant p53 may be necessary for full expression of the transforming potential of the gene.

Wild-type p53 is recognized as an important growth regulator in many cell types. Missense mutations are common for the p53 gene and are essential for the transforming ability of the oncogene. A single genetic change prompted by point mutations can create carcinogenic p53. Unlike other oncogenes, however, p53 point mutations are know to occur in at least 30 distinct codons, often creating dominant alleles that produce shifts in cell phenotype without a reduction to homozygosity. Additionally, many of these dominant negative alleles appear to be tolerated in the organism and passed on in the germ line. Various mutant alleles appear to range from minimally dysfunctional to strongly penetrant, dominant negative alleles (Weinberg, 1991).

Casey and colleagues have reported that transfection of DNA encoding wild-type p53 into two human breast cancer cell lines restores growth suppression control in such cells (Casey et al., 1991). A similar effect has also been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 is not detrimental to normal cells with endogenous wild-type p53. Thus, such constructs might be taken up by normal cells without adverse effects. It is thus proposed that the treatment of p53-associated cancers with wild-type p53 expression constructs will reduce the number of malignant cells or their growth rate. Furthermore, recent studies suggest that some p53 wild-type tumors are also sensitive to the effects of exogenous p53 expression.

The major transitions of the eukaryotic cell cycle are triggered by cyclin-dependent kinases, or CDK's. One CDK, cyclin-dependent kinase 4 (CDK4), regulates progression through the $G_1$ phase. The activity of this enzyme may be to phosphorylate Rb at late $G_I$. The activity of CDK4 is controlled by an activating subunit, D-type cyclin, and by an inhibitory subunit, e.g. $p16^{INK4}$, which has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4 inhibitor (Serrano, 1993), deletion of this gene may increase the activity of CDK4, resulting in hyperphosphorylation of the Rb protein. p16 also is known to regulate the function of CDK6.

p16INK4 belongs to a newly described class of CDK-inhibitory proteins that also includes $p16^B$, p21.sup.WAF1, CIP1, SDI1, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994a; Kamb et al., 1994b; Mori et al., 1994; Okamoto et al., 1994; Nobori et al., 1995; Orlow et al., 1994; Arap et al., 1995). Restoration of wild-type p16.sup.INK4 function by transfection with a plasmid expression vector reduced colony formation by some human cancer cell lines (Okamoto, 1994; Arap, 1995).

C-CAM is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA) (Lin and Guidotti, 1989). Using a baculovirus expression system, Cheung et al. (1993a; 1993b and 1993c) demonstrated that the first Ig domain of C-CAM is critical for cell adhesion activity.

Cell adhesion molecules, or CAMs are known to be involved in a complex network of molecular interactions that regulate organ development and cell differentiation (Edelman, 1985). Recent data indicate that aberrant expression of CAMs may be involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$. integrin by gene transfer can reduce tumorigenicity of Chinese hamster ovary cells in vivo. C-CAM now has been shown to suppress tumor growth in vitro and in vivo.

Other tumor suppressors that may be employed according to the present invention include BRCA1, BRCA2, zacl, p73, MMAC-1, ATM, HIC-1, DPC-4, FHIT, NF2, APC, DCC, PTEN, ING1, NOEY1, NOEY2, PML, OVCA1, MADR2, WT1, 53BP2, and IRF-1. Other genes that may be employed according to the present invention include Rb, APC, DCC, NF-1, NF-2, WT-1, MEN-I, MEN-II, zacl, p'73, VHL, MMAC1/PTEN, DBCCR-1, FCC, rsk-3, p2'7, p57 p27/p16 fusions, p21/p27 fusions, anti-thrombotic genes (e.g., COX-1, TFPI), PGS, Dp, E2F, ras, myc, neu, raf erb, fms, trk, ret, gsp, hst, abl, E1A, p300, genes involved in angiogenesis (e.g., VEGF, FGF, thrombospondin, BAI-1, GDAIF, or their receptors) and MCC. Inducers of apoptosis, such as Box, Bak, Bcl-X.$_S$ Bik, Bid, Harakiri, Ad E1B, Bad and ICE-CED3 proteases, similarly could find use according to the present invention.

In certain embodiments the adenovirus comprises an exogenous gene construct that is an mda-7 gene. MDA-7 is another putative tumor suppressor that has been shown to suppress the growth of cancer cells that are p53-wild-type, p53-null and p53-mutant. Also, the observed upregulation of the apoptosis-related Box gene in p53 null cells indicates that MDA-7 is capable of using p53-independent mechanisms to induce the destruction of cancer cells.

Studies have shown that elevated expression of MDA-7 suppressed cancer cell growth in vitro and selectively induced apoptosis in human breast cancer cells as well as inhibiting tumor growth in nude mice (Jiang et al., 1996 and Su et al., 1998). Jiang et al. (1996) report findings that MDA-7 is a potent growth suppressing gene in cancer cells of diverse origins including breast, central nervous system, cervix, colon, prostate, and connective tissue. A colony inhibition assay was used to demonstrate that elevated expression of MDA-7 enhanced growth inhibition in human cervical carcinoma (HeLa), human breast carcinoma (MCF-7 and T47D), colon carcinoma (LS174T and SW480), nasopharyngeal carcinoma (HONE-1), prostate carcinoma (DU-145), melanoma (H0-1 and C8161), glioblastome multiforme (GBM-18 and T98G), and osteosarcoma (Saos-2). MDA-7 overexpression in normal cells (HMECs, HBL-100, and CREF-Trans6) showed limited growth inhibition indicating that MDA7 transgene effects are not manifest in normal cells. Taken together, the data indicates that growth inhibition by elevated expression of MDA-7 is more effective in vitro in cancer cells than in normal cells. Su et al. (1998) reported investigations into the mechanism by which MDA-7 suppressed cancer cell growth. The studies reported that ectopic expression of MDA-7 in breast cancer cell lines MCF-7 and T47D induced apoptosis as detected by cell cycle analysis and TUNEL assay without an effect on the normal HBL-100 cells. Western blot analysis of cell lysates from cells infected with adenovirus MDA-7 ("Ad-MDA-7") showed an upregulation of the apoptosis stimulating protein BAX. Ad-MDA-7 infection elevated levels of BAX protein only in MCF-7 and T47D cells and not normal HBL-100 or HMEC cells. These data lead the investigators to evaluate the effect of ex vivo Ad-MDA-7 transduction on xenografi tumor formation of MCF-7 tumor cells. Ex vivo transduction resulted in the inhibition of tumor formation and progression in the tumor xenografl model. These characteristics indicate that MDA-7 has broad therapeutic, prognostic and diagnostic potential as an inducer of PKR and, consequently, an enhancer of an induced immune response.

Various enzyme genes are also considered therapeutic genes.

Particularly appropriate genes for expression include those genes that are thought to be expressed at less than normal level in the target cells of the subject mammal. Examples of particularly useful gene products include carbamoyl synthetase I, ornithine transcarbamylase, arginosuccinate synthetase, arginosuccinate lyase, and arginase. Other desirable gene products include fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione .beta.-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, .beta.-glucosidase, pyruvate carboxylase, hepatic phosphorylase, phosphorylase kinase, glycine decarboxylase (also referred to as P-protein), H-protein, T-protein, Menkes disease copper-transporting ATPase, and Wilson's disease copper-transporting ATPase. Other examples of gene products include cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase and human thymidine kinase. Hormones are another group of genes that may be used in the vectors described herein. Included are growth hormone, prolactin, placental lactogen, luteinizing hormone, follicle-stimulating hormone, chorionic gonadotropin, thyroid-stimulating hormone, leptin, adrenocorticotropin (ACTH), angiotensin I and II, β-endorphin, β-melanocyte stimulating hormone (β-MSH), cholecystokinin, endothelin I, galanin, gastric inhibitory peptide (GIP), glucagon, insulin, lipotropins, neurophysins, somatostatin, calcitonin, calcitonin gene related peptide (CGRP), β-calcitonin gene related peptide, hypercalcemia of malignancy factor (1-40), parathyroid hormone-related protein (107-139) (PTH-rP), parathyroid hormone-related protein (107-111) (PTH-rP), glucagon-like peptide (GLP-1), pancreastatin, pancreatic peptide, peptide YY, PHM, secretin, vasoactive intestinal peptide (VIP), oxytocin, vasopressin (AVP), vasotocin, enkephalinamide, metorphinamide, alpha melanocyte stimulating hormone (alpha-MSH), atrial natriuretic factor (5-28) (ANF), amylin, amyloid P component (SAP-1), corticotropin releasing hormone (CRH), growth hormone releasing factor (GRRH), luteinizing hormone-releasing hormone (LHRH), neuropeptide Y, substance K (neurokinin A), substance P and thyrotropin releasing hormone (TRH). Other classes of genes that are contemplated to be inserted into the vectors of the present invention include interleukins and cytokines. Interleukin 1 (IL-1), IL-2, IL-3, IL-4, IL-5, IL-6, IL-7, IL-8, IL-9, IL-10, IL-11 IL-12, GM-CSF and G-CSF.

Examples of diseases for which the present viral vector would be useful include, but are not limited to, adenosine deaminase deficiency, human blood clotting factor IX deficiency in hemophilia B, and cystic fibrosis, which would involve the replacement of the cystic fibrosis conductance regulator gene. The vectors embodied in the present invention could also be used for treatment of hyperproliferative disorders such as rheumatoid arthritis or restenosis by transfer of genes encoding angiogenesis inhibitors or cell cycle inhibitors. Transfer of prodrug activators such as the HSV-TK gene can be also be used in the treatment of hyperploiferative disorders, including cancer.

3. Antisense Constructs

Oncogenes such as ras, myc, neu, raf, erb, src, fms, fun, ti-k, ret, gsp, hst, bcl and abl also are suitable targets. However, for therapeutic benefit, these oncogenes would be expressed as an antisense nucleic acid, so as to inhibit the expression of the oncogene. The term "antisense nucleic acid" is intended to refer to the oligonucleotides complementary to the base sequences of oncogene-encoding DNA and RNA. Antisense oligonucleotides, when introduced into a target cell, specifically bind to their target nucleic acid and interfere with transcription, RNA processing, transport and/or translation. Targeting double-stranded (ds) DNA with oligonucleotide leads to triple-helix formation; targeting RNA will lead to double-helix formation.

Antisense constructs may be designed to bind to the promoter and other control regions, exons, introns or even exon-intron boundaries of a gene. Antisense RNA constructs, or DNA encoding such antisense R1VAs, may be employed to inhibit gene transcription or translation or both within a host cell, either in vitro or in vivo, such as within a host animal, including a human subject. Nucleic acid sequences comprising "complementary nucleotides" are those which are capable of base-pairing according to the standard Watson-Crick complementarity rules. That is, that the larger purines will base pair with the smaller pyrimidines to form only combinations of guanine paired with cytosine (G:C) and adenine paired with either thymine (A:T), in the case of DNA, or adenine paired with uracil (A:U) in the case of RNA.

As used herein, the terms "complementary" or "antisense sequences" mean nucleic acid sequences that are substantially complementary over their entire length and have very few base mismatches. For example, nucleic acid sequences of fifteen bases in length may be termed complementary when they have a complementary nucleotide at thirteen or fourteen positions with only single or double mismatches. Naturally, nucleic acid sequences which are "completely complementary" will be nucleic acid sequences which are entirely complementary throughout their entire length and have no base mismatches.

While all or part of the gene sequence may be employed in the context of antisense construction, statistically, any sequence 17 bases long should occur only once in the human genome and, therefore, suffice to specify a unique target sequence. Although shorter oligomers are easier to make and increase in vivo accessibility, numerous other factors are involved in determining the specificity of hybridization. Both binding affinity and sequence specificity of an oligonucleotide to its complementary target increases with increasing length. It is contemplated that oligonucleotides of 8, 9, 10, 11, 12, 13, 14, 15, 16, 17, 18, 19, 20 or more base pairs will be used. One can readily determine whether a given antisense nucleic acid is effective at targeting of the corresponding host cell gene simply by testing the constructs in vitro to determine whether the endogenous gene's function is affected or whether the expression of related genes having complementary sequences is affected.

In certain embodiments, one may wish to employ antisense constructs which include other elements, for example, those which include C-5 propyne pyrimidines. Oligonucleotides which contain C-5 propyne analogues of uridine and cytidine have been shown to bind RNA with high affinity and to be potent antisense inhibitors of gene expression (Wagner et al., 1993).

As an alternative to targeted antisense delivery, targeted ribozymes may be used. The term "ribozyme" refers to an RNA-based enzyme capable of targeting and cleaving particular base sequences in oncogene DNA and RNA. Ribozymes can either be targeted directly to cells, in the form of RNA oligo-nucleotides incorporating ribozyme sequences, or introduced into the cell as an expression construct encoding the desired ribozymal RNA. Ribozymes may be used and applied in much the same way as described for antisense nucleic acids.

4. Antigens for Vaccines

Other therapeutics genes might include genes encoding antigens such as viral antigens, bacterial antigens, fungal antigens or parasitic antigens. Viruses include picornavirus, coronavirus, togavirus, flavirvirus, rhabdovirus, paramyxovirus, orthomyxovirus, bunyavirus, arenvirus, reovirus, retrovirus, papovavirus, parvovirus, herpesvirus, poxvirus, hepadnavirus, and spongiform virus. Preferred viral targets include influenza, herpes simplex virus 1 and 2, measles, small pox, polio or HIV. Pathogens include trypanosomes, tapeworms, roundworms, helminths. Also, tumor markers, such as fetal antigen or prostate specific antigen, may be targeted in this manner. Preferred examples include HIV env proteins and hepatitis B surface antigen. Administration of a vector according to the present invention for vaccination purposes would require that the vector-associated antigens be sufficiently non-immunogenic to enable long term expression of the transgene, for which a strong immune response would be desired. Preferably, vaccination of an individual would only be required infrequently, such as yearly or biennially, and provide long term immunologic protection against the infectious agent.

5. Control Regions

In order for the viral vector to effect expression of a transcript encoding a therapeutic gene, the polynucleotide encoding the therapeutic gene will be under the transcriptional control of a promoter and a polyadenylation signal. Therefore, certain embodiments of the present invention involve methods for producing an adenovirus wherein the adenovirus comprises an adenoviral vector encoding an exogenous gene construct that is operatively linked to a promoter. A "promoter" refers to a DNA sequence recognized by the synthetic machinery of the host cell, or introduced synthetic machinery, that is required to initiate the specific transcription of a gene. A polyadenylation signal refers to a DNA sequence recognized by the synthetic machinery of the host cell, or introduced synthetic machinery, that is required to direct the addition of a series of nucleotides on the end of the mRNA transcript for proper processing and trafficking of the transcript out of the nucleus into the cytoplasm for translation. The phrases "operatively linked," "under control," and "under transcriptional control" mean that the promoter is in the correct location in relation to the polynucleotide to control RNA polymerase initiation and expression of the polynucleotide.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a therapeutic gene is not believed to be critical, so long as it is capable of expressing the polynucleotide in the targeted cell. The promoter may be a tissue-specific promoter or an inducible promoter. Examples of promoters that may be employed include SV40 E1, RSV LTR, β-actin, CMV-LE, adenovirus major late, polyoma F9-1, α-fetal protein promoter, egr-1, or tyrosinase promoter. One of skill in the art would be familiar with the range of options available for promoters that can be used to control the expression of a therapeutic gene. Thus, where a human cell is targeted, it is preferable to position the polynucleotide coding region adjacent to and under the control of a promoter that is capable of being expressed in a human cell. Generally speaking, such a promoter might include either a human or viral promoter. A list of promoters is provided in the Table 2.

TABLE 2

| PROMOTER |
| --- |
| Immunoglobulin Heavy Chain |
| Immunoglobulin Light Chain |
| T-Cell Receptor |
| HLA DQ α and DQ β |

TABLE 2-continued

| PROMOTER |
| --- |
| β-Interferon |
| Interleukin-2 |
| Interleukin-2 Receptor |
| MHC Class II 5 |
| MHC Class II HLA-DRα |
| β-Actin |
| Muscle Creatine Kinase |
| Prealbumin (Transthyretin) |
| Elastase I |
| Metallothionein |
| Collagenase |
| Albumin Gene |
| α-Fetoprotein |
| τ-Globin |
| β-Globin |
| c-fos |
| c-HA-ras |
| Insulin |
| Neural Cell Adhesion Molecule (NCAM) |
| α1-Antitrypsin |
| H2B (TH2B) Histone |
| Mouse or Type I Collagen |
| Glucose-Regulated Proteins (GRP94 and GRP78) |
| Rat Growth Hormone |
| Human Serum Amyloid A (SAA) |
| Troponin I (TN I) |
| Platelet-Derived Growth Factor |
| Duchenne Muscular Dystrophy |
| SV40 |
| Polyoma |
| Retroviruses |
| Papilloma Virus |
| Hepatitis B Virus |
| Human Immunodeficiency Virus |
| Cytomegalovirus |
| Gibbon Ape Leukemia Virus |

The promoter may be a constitutive promoter, an inducible promoter, or a tissue-specific promoter. An inducible promoter is a promoter which is inactive or exhibits low activity except in the presence of an inducer substance. Some examples of promoters that may be included as a part of the present invention include, but are not limited to, MT II, MMTV, Collagenase, Stromelysin, SV40, Murine MX gene, α-2-Macroglobulin, MHC class I gene h-2kb, HSP70, Proliferin, Tumor Necrosis Factor, or Thyroid Stimulating Hormone α gene. The associated inducers are shown in Table 3. It is understood that any inducible promoter may be used in the practice of the present invention and that all such promoters would fall within the spirit and scope of the claimed invention. A promoter that is "endogenous" or "constitutive" is a promoter that is one naturally associated with a gene or sequence, as may be obtained by isolating the 5' non-coding sequences located upstream of the coding segment and/or exon.

TABLE 3

| Element | Inducer |
| --- | --- |
| MT II | Phorbol Ester (TPA) |
|  | Heavy metals |
| MMTV (mouse mammary tumor virus) | Glucocorticoids |
| β-Interferon | poly(rI)X |
|  | poly(rc) |
| Adenovirus 5 E2 | E1a |
| c-jun | Phorbol Ester (TPA), $H_2O_2$ |
| Collagenase | Phorbol Ester (TPA) |
| Stromelysin | Phorbol Ester (TPA), IL-1 |
| SV40 | Phorbol Ester (TPA) |
| Murine MX Gene | Interferon, Newcastle Disease Virus |

TABLE 3-continued

| Element | Inducer |
|---|---|
| GRP78 Gene | A23187 |
| α-2-Macroglobulin | IL-6 |
| Vimentin | Serum |
| MHC Class I Gene H-2kB | Interferon |
| HSP70 | Ela, SV40 Large T Antigen |
| Proliferin | Phorbol Ester-TPA |
| Tumor Necrosis Factor | FMA |
| Thyroid Stimulating Hormone α Gene | Thyroid Hormone |

In various elements, the human cytomegalovirus (CMV) immediate early gene promoter, the SV40 early promoter and the Rous sarcoma virus long terminal repeat can be used to obtain high-level expression of the polynucleotide of interest. The use of other viral or mammalian cellular or bacterial phage promoters which are well-known in the art to achieve expression of polynucleotides is contemplated as well, provided that the levels of expression are sufficient to produce a growth inhibitory effect.

By employing a promoter with well-known properties, the level and pattern of expression of a polynucleotide following transfection can be optimized. For example, selection of a promoter which is active in specific cells, such as tyrosinase (melanoma), alpha-fetoprotein and albumin (liver tumors), CC10 (lung tumor) and prostate-specific antigen (prostate tumor) will permit tissue-specific expression of the therapeutic gene.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the eukaryotic Promoter Data Base (EPDB)) could also be used to drive expression of a particular construct. Use of a T3, T7 or SP6 cytoplasmic expression system is another possible embodiment. Eukaryotic cells can support cytoplasmic transcription from certain bacteriophage promoters if the apropriate bacteriophage polymerase is provided, either as part of the delivery complex or as an additional genetic expression vector.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed. Such polyadenylation signals as that from SV40, bovine growth hormone, and the herpes simplex virus thymidine kinase gene have been found to function well in a number of target cells.

F. Methods of Isolating Adenovirus

Adenoviral infection results in the lysis of the cells being infected. The lytic characteristics of adenovirus infection permit two different modes of virus isolation and production. One is harvesting infected cells prior to cell lysis. The other mode is harvesting virus supernatant after complete cell lysis by the produced virus. For the latter mode, longer incubation times are required in order to achieve complete cell lysis. This prolonged incubation time after virus infection creates a serious concern about increased possibility of generation of replication competent adenovirus (RCA), particularly for the current first generation adenoviral vectors (E1-deleted vector). Therefore, in certain embodiments of the present invention, the methods for producing an a denovirus involve harvesting the host cells and then lysing the host cells. Table 4 lists the most common methods that have been used for lysing cells after cell harvest.

TABLE 4

| Methods used for cell lysis | | |
|---|---|---|
| Methods | Procedures | Comments |
| Freeze-thaw | Cycling between dry ice and 37° C. water bath | Easy to carry out at lab scale. High cell lysis efficiency Not scaleable Not recommended for large scale manufacturing |
| Solid Shear | French Press Hughes Press | Capital equipment investment Virus containment concerns Lack of experience |
| Detergent lysis | Non-ionic detergent solutions such as Tween ®, Triton ®, NP-40, etc. | Easy to carry out at both lab and manufacturing scale Wide variety of detergent choices Concerns of residual detergent in finished product |
| Hypotonic solution lysis | water, citric buffer | Low lysis efficiency |
| Liquid Shear | Homogenizer Impinging Jet Microfluidizer | Capital equipment investment Virus containment concerns Scaleability concerns |
| Sonication | ultrasound | Capital equipment investment Virus containment concerns Noise pollution Scaleability concern |

1. Detergents

In certain embodiments of the present invention, the methods for producing an adenovirus involve isolating the adenovirus by lysing the host cells with a detergent. Cells are bounded by membranes. In order to release components of the cell, it is necessary to break open the cells. The most advantageous way in which this can be accomplished, according to the present invention, is to solubilize the membranes with the use of detergents. Detergents are amphipathic molecules with an apolar end of aliphatic or aromatic nature and a polar end which may be charged or uncharged. Detergents are more hydrophilic than lipids and thus have greater water solubility than lipids. They allow for the dispersion of water insoluble compounds into aqueous media and are used to isolate and purify proteins in a native form.

Any detergent capable of lysing the host cells is contemplated by the claimed invention. One of skill in the art would be familiar with the wide range of detergents available for lysing cells. Detergents can be denaturing or non-denaturing. The former can be anionic such as sodium dodecyl sulfate or cationic such as ethyl trimethyl ammonium bromide. These detergents totally disrupt membranes and denature the protein by breaking protein-protein interactions. Non denaturing detergents can be divided into non-anionic detergents such as TRITON® X-100, bile salts such as cholates and zwitterionic detergents such as CHAPS. Zwitterionics contain both cationic and anion groups in the same molecule, the positive electric charge is neutralized by the negative charge on the same or adjacent molecule.

Denaturing agents such as SDS bind to proteins as monomers and the reaction is equilibrium driven until saturated. Thus, the free concentration of monomers determines the necessary detergent concentration. SDS binding is cooperative i.e. the binding of one molecule of SDS increase the probability of another molecule binding to that protein, and alters proteins into rods whose lengths is proportional to their molecular weight.

Non-denaturing agents such as TRITON® X-100 do not bind to nativeconformations nor do they have a cooperative binding mechanism. These detergents have rigid and bulky apolar moieties that do not penetrate into water soluble proteins. They bind to the hydrophobic parts of proteins. TRITON® X100 and other polyoxyethylene nonanionic detergents are inefficient in breaking protein-protein interaction and can cause artifactual aggregations of protein. These detergents will, however, disrupt protein-lipid interactions but are much gentler and capable of maintaining the native form and functional capabilities of the proteins.

Detergent removal can be attempted in a number of ways. Dialysis works well with detergents that exist as monomers. Dialysis is somewhat ineffective with detergents that readily aggregate to form micelles because they micelles are too large to pass through dialysis. Ion exchange chromatography can be utilized to circumvent this problem. The disrupted protein solution is applied to an ion exchange chromatography column and the column is then washed with buffer minus detergent. The detergent will be removed as a result of the equilibration of the buffer with the detergent solution. Alternatively the protein solution may be passed through a density gradient. As the protein sediments through the gradients the detergent will come off due to the chemical potential.

Often a single detergent is not versatile enough for the solubilization and analysis of the milieu of proteins found in a cell. The proteins can be solubilized in one detergent and then placed in another suitable detergent for protein analysis. The protein detergent micelles formed in the first step should separate from pure detergent micelles. When these are added to an excess of the detergent for analysis, the protein is found in micelles with both detergents. Separation of the detergent-protein micelles can be accomplished with ion exchange or gel filtration chromatography, dialysis or buoyant density type separations.

a. TRITON® X-Detergents

This family of detergents (TRITON® X-100, X114 and NP-40) have the same basic characteristics but are different in their specific hydrophobic-hydrophilic nature. All of these heterogeneous detergents have a branched 8-carbon chain attached to an aromatic ring. This portion of the molecule contributes most of the hydrophobic nature of the detergent. TRITON® X detergents are used to solublize membrane proteins under non-denaturing conditions. The choice of detergent to solubilize proteins will depend on the hydrophobic nature of the protein to be solubilized. Hydrophobic proteins require hydrophobic detergents to effectively solubilize them.

TRITON® X-100 and NP-40 are very similar in structure and hydrophobicity and are interchangeable in most applications including cell lysis, delipidation protein dissociation and membrane protein and lipid solubilization. Generally 2 mg of detergent is used to solubilize 1 mg membrane protein or 10 mg detergent/1 mg of lipid membrane. TRITON® X-114 is useful for separating hydrophobic from hydrophilic proteins.

b. BRIJ® Detergents

These are similar in structure to TRITON® X detergents in that they have varying lengths of polyoxyethylene chains attached to a hydrophobic chain. However, unlike TRITON® X detergents, the BRIJ® detergents do not have an aromatic ring and the length of the carbon chains can vary. The BRIJ detergents are difficult to remove from solution using dialysis but may be removed by detergent removing gels. BRIJ® 58 is most similar to TRITON® 100 in its hydrophobic/hydrophilic characteristics. BRIJ®-35 is a commonly used detergent in HPLC applications.

c. Dialyzable Nonionic Detergents

η-Octyl-13-D-glucoside (octylglucopyranoside) and ThOctyl-P-D-thioglucoside (octylthioglucopyranoside, OTG) are nondenaturing nonionic detergents which are easily dialyzed from solution. These detergents are useful for solubilizing membrane proteins and have low UV absorbances at 280 nm. Octylglucoside has a high CMC of 23-25 mM and has been used at concentrations of 1.1-1.2% to solubilize membrane proteins.

Octylthioglucoside was first synthesized to offer an alternative to octylglucoside. Octylglucoside is expensive to manufacture and there are some inherent problems in biological systems because it can be hydrolyzed by β-glucosidase.

d. TWEEN® Detergents

The TWEEN® detergents are nondenaturing, nonionic detergents. They are polyoxyethylene sorbitan esters of fatty acids. TWEEN® 20 and TWEEN® 80 detergents are used as blocking agents in biochemical applications and are usually added to protein solutions to prevent nonspecific binding to hydrophobic materials such as plastics or nitrocellulose. They have been used as blocking agents in ELISA and blotting applications. Generally, these detergents are used at concentrations of 0.01-1.0% to prevent nonspecific binding to hydrophobic materials.

TWEEN® 20 and other nonionic detergents have been shown to remove some proteins from the surface of nitrocellulose. TWEEN® 80 has been used to solubilize membrane proteins, present nonspecific binding of protein to multiwell plastic tissue culture plates and to reduce nonspecific binding by serum proteins and biotinylated protein A to polystyrene plates in ELISA.

The difference between these detergents is the length of the fatty acid chain. TWEEN® 80 is derived from oleic acid with a $C_{18}$ chain while TWEEN® 20 is derived from lauric acid with a $C_{12}$ chain. The longer fatty acid chain makes the TWEEN® 80 detergent less hydrophilic than TWEEN® 20 detergent. Both detergents are very soluble in water.

The TWEEN® detergents are difficult to remove from solution by dialysis, but TWEEN® 20 can be removed by detergent removing gels. The polyoxyethylene chain found in these detergents makes them subject to oxidation (peroxide formation) as is true with the TRITON® X and BRIJ® series detergents.

e. Zwitterionic Detergents

The zwitterionic detergent, CHAPS, is a sulfobetaine derivative of cholic acid. This zwitterionic detergent is useful for membrane protein solubilization when protein activity is important. This detergent is useful over a wide range of pH (pH 2-12) and is easily removed from solution by dialysis due to high CMCs (8-10 mM). This detergent has low absorbances at 280 nm making it useful when protein monitoring at this wavelength is necessary. CHAPS is compatible with the BCA Protein Assay and can be removed from solution by detergent removing gel. Proteins can be iodinated in the presence of CHAPS.

CHAPS has been successfully used to solubilize intrinsic membrane proteins and receptors and maintain the functional capability of the protein. When cytochrome P-450 is solubilized in either TRITON® X-100 or sodium cholate aggregates are formed.

2. Non-Detergent Methods

Various non-detergent methods, though not preferred, may be employed in conjunction with other advantageous aspects of the present invention:

a. Freeze-Thaw

This has been a widely used technique for lysis cells in a gentle and effective manner. Cells are generally frozen rapidly in, for example, a dry ice/ethanol bath until completely frozen, then transferred to a 37° C. bath until completely thawed. This cycle is repeated a number of times to achieve complete cell lysis.

b. Sonication

High frequency ultrasonic oscillations have been found to be useful for cell disruption. The method by which ultrasonic waves break cells is not fully understood but it is known that high transient pressures are produced when suspensions are subjected to ultrasonic vibration. The main disadvantage with this technique is that considerable amounts of heat are generated. In order to minimize heat effects specifically designed glass vessels are used to hold the cell suspension. Such designs allow the suspension to circulate away from the ultrasonic probe to the outside of the vessel where it is cooled as the flask is suspended in ice.

c. High Pressure Extrusion

This is a frequently used method to disrupt microbial cell. The French pressure cell employs pressures of $10.4 \times 10^7$ Pa (16,000 p.s.i.) to break cells open. These apparatus consists of a stainless steel chamber which opens to the outside by means of a needle valve. The cell suspension is placed in the chamber with the needle valve in the closed position. After inverting the chamber, the valve is opened and the piston pushed in to force out any air in the chamber. With the valve in the closed position, the chamber is restored to its original position, placed on a solid based and the required pressure is exerted on the piston by a hydraulic press. When the pressure has been attained the needle valve is opened fractionally to slightly release the pressure and as the cells expand they burst. The valve is kept open while the pressure is maintained so that there is a trickle of ruptured cell which may be collected.

d. Solid Shear Methods

Mechanical shearing with abrasives may be achieved in Mickle shakers which oscillate suspension vigorously (300-3000 time/min) in the presence of glass beads of 500 nm diameter. This method may result in organelle damage. A more controlled method is to use a Hughes press where a piston forces most cells together with abrasives or deep frozen paste of cells through a 0.25 mm diameter slot in the pressure chamber. Pressures of up to $5.5 \times 10^7$ Pa (8000 p.s.i.) may be used to lyse bacterial preparations.

e. Liquid Shear Methods

These methods employ blenders, which use high speed reciprocating or rotating blades, homogenizers which use an upward/downward motion of a plunger and ball and microfluidizers or impinging jets which use high velocity passage through small diameter tubes or high velocity impingement of two fluid streams. The blades of blenders are inclined at different angles to permit efficient mixing. Homogenizers are usually operated in short high speed bursts of a few seconds to minimize local heat. These techniques are not generally suitable for microbial cells but even very gentle liquid shear is usually adequate to disrupt animal cells.

f. Hypotonic/Hypertonic Methods

Cells are exposed to a solution with a much lower (hypotonic) or higher (hypertonic) solute concentration. The difference in solute concentration creates an osmotic pressure gradient. The resulting flow of water into the cell in a hypotonic environment causes the cells to swell and busrt. The flow of water out of the cell in a hypertonic environment causes the cells to shrink and subsequently burst.

G. Methods of Concentration and Filtration

The present invention involve methods of producing an adenovirus that involve isolating the adenovirus. Methods of isolating the adenovirus from host cells include any methods known to those of skill in the art. For example, these methods may include clarification, concentration and diafiltration. One step in the purification process can include clarification of the cell lysate to remove large particulate matter, particularly cellular components, from the cell lysate. Clarification of the lysate can be achieved using a depth filter or by tangential flow filtration. In one embodiment of the present invention, the cell lysate is concentrated. Concentrating the crude cell lysate may include any step known to those of skill in the art. For example, the crude cell lysate may be passed through a depth filter, which consists of a packed column of relatively non-adsorbent material (e.g. polyester resins, sand, diatomeceous earth, colloids, gels, and the like). In tangential flow filtration (TFF), the lysate solution flows across a membrane surface which facilitates back diffusion of solute from the membrane surface into the bulk solution. Membranes are generally arranged within various types of filter apparatus including open channel plate and frame, hollow fibers, and tubules.

After clarification and prefiltration of the cell lysate, the resultant virus supernatant may be concentrated and buffer may be exchanged by diafiltration. The virus supernatant can be concentrated by tangential flow filtration across an ultrafiltration membrane of 100-300K nominal molecular weight cutoff. Ultrafiltration is a pressure-modified convective process that uses semi-permeable membranes to separate species by molecular size, shape and/or charge. It separates solvents from solutes of various sizes, independent of solute molecular size. Ultrafiltration is gentle, efficient and can be used to simultaneously concentrate and desalt solutions. Ultrafiltration membranes generally have two distinct layers: a thin (0.1-1.5 pm), dense skin with a pore diameter of 10-400 angstroms and an open substructure of progressively larger voids which are largely open to the permeate side of the ultrafilter. Any species capable of passing through the pores of the skin can therefore freely pass through the membrane. For maximum retention of solute, a membrane is selected that has a nominal molecular weight cut-off well below that of the species being retained. In macromolecular concentration, the membrane enriches the content of the desired biological species and provides filtrate cleared of retained substances. Microsolutes are removed convectively with the solvent. As concentration of the retained solute increases, the ultrafiltration rate diminishes.

Some embodiments of the present invention involve use of exchanging buffer of the crude cell lysate. Buffer exchange, or diafiltration, involves using ultrafilters is an ideal way for removal and exchange of salts, sugars, non-aqueous solvents separation of free from bound species, removal of material of low molecular weight, or rapid change of ionic and pH environments. Microsolutes are removed most efficiently by adding solvent to the solution being ultrafiltered at a rate equal to the ultrafiltration rate. This washes microspecies from the solution at constant volume, purifying the retained species.

H. Removing Nucleic Acid Contaminants

Certain embodiments of the methods for producing an adenovirus involve reducing the concentration of contaminating nucleic acids in a crude cell lysate. The present invention employs nucleases to remove contaminating nucleic acids. Exemplary nucleases include BENZONASE®, PULMOZYME®; or any other DNase or RNase commonly used within the art.

Enzymes such as BENZONASE® degrade nucleic acid and have no proteolytic activity. The ability of BENZONASE® to rapidly hydrolyze nucleic acids makes the enzyme ideal for reducing cell lysate viscosity. It is well known that nucleic acids may adhere to cell derived particles such as viruses. The adhesion may interfere with separation due to agglomeration, change in size of the particle or change in particle charge, resulting in little if any product being recovered with a given purification scheme. BENZONASE® is well suited for reducing the nucleic acid load during purification, thus eliminating the interference and improving yield.

As with all endonucleases, BENZONASE® hydrolyzes internal phosphodiester bonds between specific nucleotides. Upon complete digestion, all free nucleic acids present in solution are reduced to oligonucleotides 2 to 4 bases in length.

I. Size Partitioning Purification

According to one aspect of the invention it has been found that size partitioning purification techniques may be used to provide adenoviral preparations of sufficient purity that they may be therapeutically administered without additional purification steps such as chromatographic and other methods previously considered necessary. Without intending to be bound by any particular theory of the invention it is believed that the steps of processing viral host cells in a cell suspension culture in a serum free media results in a viral particle product with a reduced load of contaminants. Moreover, the contaminants are of a size and nature that they may be readily separated from viral particles by a simple size partitioning purification step.

Membrane filtration is a well known technique in the art of bioprocessing. A membrane is defined as a structure having lateral dimensions much greater than its thickness, through which mass transfer may occur under a variety of driving forces. While many filters are may be considered membranes, filters also include materials whose lateral dimensions are not usually 100 times greater than their depth and whose separation function is primarily by capture of species or particles through their depth. The most common parameters used to characterize membranes fall in three general categories. These are transport properties, pore (geometric) characteristics, and surface (or predominantely chemical) properties. Nevertheless, the transport properties depend significantly upon the pore and surface characteristics. While membrane separation can be slower and a lower volume process than other separton processes, its effectiveness makes it a preferred method for retrieving small amounts of valuable products.

Membrane filter systems may be designed in a variety of manners to have different filtration properties. Design criteria include: operation in dead-end (with or without stirring) or cross flow mode; full or partial recovery of the feed mixture; application of an external transmembrane pressure via pumping, inert gas blanket, or evacuation of the permeate side of the device; and the use of flat sheets (either singly or multiply), hollow fiber bundle, or tubular membranes. Preferred size partitioning separation methods utilize a size partitioning membrane which may be a dialysis or other similar membrane as would be known to those of ordinary skill in the art. Suitable dialysis membrane materials useful in the size partitioning membrane filtration fo the invention include those commercially available such as those produced from polyethersulphone, polycarbonate, nylon, polypropylene and the like. Suppliers of these dialysis membrane materials include Akzo-Nobel, Millipore, Inc., Poretics, Inc., and Pall Corp., by way of example. Size partitioning membranes having pore sizes of less than 0.08 microns are useful in practice of the invention with those having pore sizes less than 0.05 microns and less than 0.02 microns and greater than 0.001 microns being particularly preferred. Such membranes are capable of allowing the passage of desired viral particles while retaining undesired contaminants.

According to one aspect of the invention, tangential flow filtration (TFF) units, also known as "cross-flow filtration", have been found to be particularly advantageous for practice of the invention. Tangential flow filtration is a pressure driven separation process wherein fluid is pumped tangentially long the surface of a membrane. An applied pressure serves to force a portion of the fluid including contaminants through the membrane to the filtrate size. Particulates and macromolecules that are too large to pass through the membrane pores are retained on the upstream side. In contrast to normal flow filtration (NFF) techniques in which the retained components build up on the surface of the membrane, tangential flow filtration sweeps the retained components along by the flow of the fluid.

TFF is classified based on the size of components being separated. A membrane pore size rating is typically given as a micron value and indicates that particles larger than the rating will be retained by the membrane. A nominal molecular weight limit (NMWL), on the other hand, is an indication that most dissolved macromolecules with molecular weights higher than the NMWL and some with molecular weights lower than the NMWL will be retained by the membrane. A component's shape, its ability to deform, and its interaction with other components in the solution all affect retention. Different membrane manufacturers use different criteria to assign the NMWL ratings to a family of membranes but those of ordinary skill would be able to determine the appropriate rating empirically.

Ultrafiltration is one of the most widely used forms of TFF and is used to separate proteins from buffer components for buffer exchange, desalting or concentration but may also be used for Virus Filtration range from 100 kD to 500 kD, or up to 0.05 to 0.08 microns.

Diafiltration is a TFF process than can be performed in combination with any of the other categories of separation to enhance either produce yield or purity. During diafiltration, buffer is introduced into the recycle tank while filtrate is removed from the unit operation. In processes where the product is in the retentate, diafiltration washes components out of the product pool into the filtrate, thereby exchanging buffers and reducing the concentration of undesirable species. When the product is in the filtrate, diafiltration washes it through the membrane into a collection vessel.

In TFF unit operation, a pump is used to generate flow of the feed stream through the channel between two membrane surfaces. During each pass of fluid over the surface of the membrane, the applied pressure forces a portion of the fluid through the membrane and into the filtrate stream. The result is a gradient in the feedstock concentration from the bulk conditions at the center of the channel to the more concentrated wall conditions at the membrane surface. There is also a concentration gradient along the length of the feed channel from the inlet to the outlet (retentate) at progressively more fluid passes to the filtrate side. The flow of feedstock along the length of the membrane causes a pressure drop from the feed to the retentate end of the channel. The flow on the filtrate side of the membrane is typically low and there is little restriction, so the pressure along the length of the membrane on the filtrate side is approximately constant.

Membranes may be fabricated from various materials offering alternatives in flushing characteristics and chemical compatibility. Suitable materials include cellulose, polyethersulfone and other materials known to those of skill in the art with polyethersulfone being particularly preferred. Typical polyethersulfone membranes tend to adsorb protein as well as other biological components, leading to membrane fouling and lowered flux. Some membranes are hydrophilitcally modified to be more resistant to fouling such as Biomax® (Millipore).

Those of skill in the art would recognize that various types of TFF modules would be useful in practice of the invention. Useful TFF modules include but are not limited to flat plate modules (also known as cassettes), spiral wound modules, and hollow fiber modules. In flat plate modules, layers of membrane either with or without alternating layers of separator screen are stacked together and then sealed into a package. Feed fluid is pumped into alternating channels at one end of the stack and the filtrate passes through the membrane into the filtrate channels. Flat plat modules generally have high packing densities (area of membrane surface per area of floor space), allow linear scaling, and some offer the choice of open or turbulence promoted channels.

Spiral wound modules comprise alternating layers of membrane and separator screen wound around a hollow central core. the feed stream is pumped into one end and flows down the axis of the cartridge. Filtrate passes through the membrane and spirals to the core, where it is removed. The separator screens increase turbulence in the flowpath, leading to a higher efficiency module than hollow fibers. One drawback to spiral wound modules is that they are not linearly scaleable because either the feed flowpath length (cartridge length) or the filtrate flowpath length (cartridge width) must be changed within scales.

Hollow fiber modules are comprises of a bundle of membrane tubes with narrow diameters (typically in the range of 0.1 to 2.0 mm). In a hollow fiber module, the feed stream is pumped into the lumen (inside) of the tube and the filtrate passes through the membrane to the shell side, where it is removed. Because of the very open feed flowpath, low shear is generated even with moderate cross flow rates.

For any given module, key process parameters may then be readily optimized by those of ordinary skill. Such parameters include cross flow rate, transmembrane pressure (TMP), filtrate control, membrane area and diafiltration design. Cross flow rate depends upon which module is selected. In general, a higher cross flow rate gives higher flux at equal TMP and increases the sweeping action across the membrane and reduces the concentration gradient towards the membrane surface. Many TFF applications apply a cross flow and pressure set point and the filtrate flows uncontrolled and unrestricted out of the module. This is the simplest type of operation but in some circumstances it might be desired to use some type of filtrate control beyond that achieved by simply adjusting the pressure with the retentate valve. Membrane area is selected after determining the process flow and the total volume to be processed and is also dependent upon process time.

According to one aspect of the invention a plate and frame TFF system was used with each of a 300 KD, a 500 KD or a 1000 KD polysulfone membrane having a surface area of 1.1 ft$^2$. The cross flow rate was 900 mL/ft$^2$/min. and the transmembrane pressure was about 7 psi. The filtrate rate was not actively controlled and the diafiltration was performed using the consistent volume method.

The invention provides methods of producing purified adenovirus compositions which avoid the necessity of multiple purification steps including chromatographic purification steps. Nevertheless, additional purification steps including those known to the art may be practiced if desired. Such methods include those taught in U.S. Pat. No. 6,194,191, the disclosure of which is incorporated by reference, including density gradient centrifugation; chromatography including size exclusion chromatography, ion exchange chromatography (HPLC), and the like.

J. Pharmaceutical Formulations

The present invention includes, in certain embodiments, methods for producing an adenovirus that involve placing the adenovirus into a pharmaceutically acceptable composition. The present invention also includes compositions of adenovirus prepared by one of the processes disclosed herein, wherein the composition is a pharmaceutically acceptable composition.

When purified according to the methods set forth above, the viral particles of the present invention will be administered in various manners with in vitro, ex vivo or in vivo being contemplated. Thus, it will be desirable to prepare the complex as a pharmaceutical composition appropriate for the intended application. Generally this will entail preparing a pharmaceutical composition that is essentially free of pyrogens, as well as any other impurities that could be harmful to humans or animals. It may also be desired to employ appropriate salts and buffers to render the complex stable and allow for complex uptake by target cells.

The phrase "pharmaceutically acceptable composition" refers to molecular entities and compositions that do not produce an adverse, allergic or other untoward reaction when administered to an animal, or a human, as appropriate. As used herein, "pharmaceutically acceptable composition" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients also can be incorporated into the composition. In addition, the composition can include supplementary inactive ingredients. For instance, the composition for use as a mouthwash may include a flavorant or the composition may contain supplementary ingredients to make the formulation timed-release.

Aqueous compositions of the present invention comprise an effective amount of the expression cassette, dissolved or dispersed in a pharmaceutically acceptable carrier or aqueous medium. Such compositions also are referred to as inocula. Examples of aqueous compositions include a formulation for intravenous administration or a formulation for topical application.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, there preparations contain a preservative to prevent the growth of microorganisms.

The viral particles of the present invention may include classic pharmaceutical preparations for use in therapeutic regimens, including their administration to humans. Administration of therapeutic compositions according to the present invention will be via any common route so long as the target tissue is available via that route. This includes oral, nasal, buccal, rectal, vaginal or topical. Alternatively, administration may be by orthotopic, intradermal subcutaneous, intramuscular, intraperitoneal, or intravenous injection. Such compositions would normally be administered as pharmaceutically acceptable compositions that include physiologically acceptable carriers, buffers or other excipients. For application against tumors, direct intratumoral injection, inject of a resected tumor bed, regional (i.e., lymphatic) or general administration is contemplated. It also may be desired to perform continuous perfusion over hours or days via a catheter to a disease site, e.g., a tumor or tumor site.

The therapeutic and preventive compositions of the present invention are advantageously administered in the form of liquid solutions or suspensions; solid forms suitable for solution in, or suspension in, liquid prior to topical use may also be prepared. A typical composition for such purpose comprises a pharmaceutically acceptable carrier. For instance, the composition may contain 10 mg, 25 mg, 50 mg or up to about 100 mg of human serum albumin per ml of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Preservatives include antimicrobial agents, anti-oxidants, chelating agents and inert gases. The pH and exact concentration of the various components of the pharmaceutical composition are adjusted according to well-known parameters.

Oral formulations include such normally employed excipients as, for example, pharmaceutical grades of mannitol, lactose, starch, magnesium stearate, sodium saccharine, cellulose, magnesium carbonate and/or the like. These compositions take the form of solutions such as mouthwashes and mouthrinses, suspensions, tablets, pills, capsules, sustained release formulations and/or powders. In certain defined embodiments, oral pharmaceutical compositions will comprise an inert diluent and/or assimilable edible carrier, and/or they may be enclosed in hard and/or soil shell gelatin capsule, and/or they may be compressed into tablets, and/or they may be incorporated directly with the food of the diet. For oral therapeutic administration, the active compounds may be incorporated with excipients and/or used in the form of ingestible tablets, buccal tables, troches, capsules, elixirs, suspensions, syrups, wafers, and/or the like. Such compositions and/or preparations should contain at least 0.1% of active compound. The percentage of the compositions and/or preparations may, of course, be varied and/or may conveniently be between about 2 to about 75% of the weight of the unit, and/or preferably between 25-60%. The amount of active compounds in such therapeutically useful compositions is such that a suitable dosage will be obtained.

The tablets, troches, pills, capsules and/or the like may also contain the following: a binder, as gum tragacanth, acacia, cornstarch, and/or gelatin; excipients, such as dicalcium phosphate; a disintegrating agent, such as corn starch, potato starch, alginic acid and/or the like; a lubricant, such as magnesium stearate; and/or a sweetening agent, such as sucrose, lactose and/or saccharin may be added and/or a flavoring agent, such as peppermint, oil of wintergreen, and/or cherry flavoring. When the dosage unit form is a capsule, it may contain, in addition to materials of the above type, a liquid carrier. Various other materials may be present as coatings and/or to otherwise modify the physical form of the dosage unit. For instance, tablets, pills, and/or capsules may be coated with shellac, sugar and/or both. A syrup of elixir may contain the active compounds sucrose as a sweetening agent methyl and/or propylparabens as preservatives, a dye and/or flavoring, such as cherry and/or orange flavor.

For oral administration the expression cassette of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

One may also use solutions and/or sprays, hyposprays, aerosols and/or inhalants in the present invention for administration. One example is a spray for administration to the aerodigestive tract. The sprays are isotonic and/or slightly buffered to maintain a pH of 5.5 to 6.5. In addition, antimicrobial preservatives, similar to those used in ophthalmic preparations, and/or appropriate drug stabilizers, if required, may be included in the formulation. Additional formulations which are suitable for other modes of administration include vaginal or rectal suppositories and/or pessaries. Formulations for other types of administration that is topical include, for example, a cream, suppository, ointment or salve.

An effective amount of the therapeutic agent is determined based on the intended goal, for example (i) inhibition of tumor cell proliferation, (ii) elimination or killing of tumor cells, (iii) vaccination, or (iv) gene transfer for long term expression of a therapeutic gene. The term "unit dose" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the subject to be treated, the state of the subject and the result desired. Multiple gene therapeutic regimens are expected, especially for adenovirus.

In certain embodiments of the present invention, an adenoviral vector encoding a tumor suppressor gene will be used to treat cancer patients. Typical amounts of an adenovirus vector used in gene therapy of cancer is $10^3$-$10^{15}$ PFU/dose, ($10^3$, $10^4$, $10^5$, $10^6$, $10^7$, $10^8$, $10^9$, $10^{10}$, $10^{11}$ $10^{12}$, $10^{13}$, $10^{14}$, $10^{15}$) wherein the dose may be divided into several injections at different sites within a solid tumor. The treatment regimen also may involve several cycles of administration of the gene transfer vector over a period of 3-10 weeks. Administration of the vector for longer periods of time from months to years may be necessary for continual therapeutic benefit.

In another embodiment of the present invention, an adenoviral vector encoding a therapeutic gene may be used to vaccinate humans or other mammals. Typically, an amount of virus effective to produce the desired effect, in this case vaccination, would be administered to a human or mammal so that long term expression of the transgene is achieved and a strong host immune response develops. It is contemplated that a series of injections, for example, a primary injection followed by two booster injections, would be sufficient to induce an long term immune response. A typical dose would be from 106 to 1015 PFU/injection depending on the desired result. Low doses of antigen generally induce a strong cell-mediated response, whereas high doses of antigen generally induce an antibody-mediated immune response. Precise amounts of the therapeutic composition also depend on the judgment of the practitioner and are peculiar to each individual.

Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Figure 3:
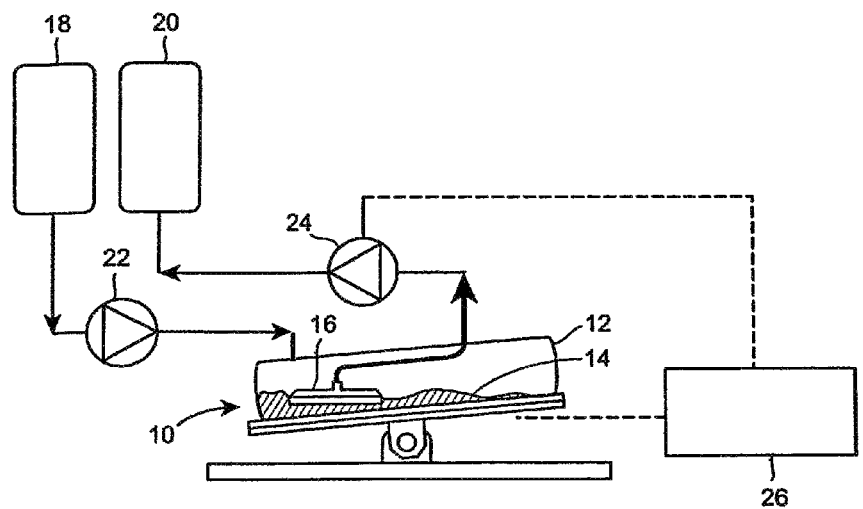
FIG. 3 depicts a diagram of a perfusion bioreactor system.
Figure 4:
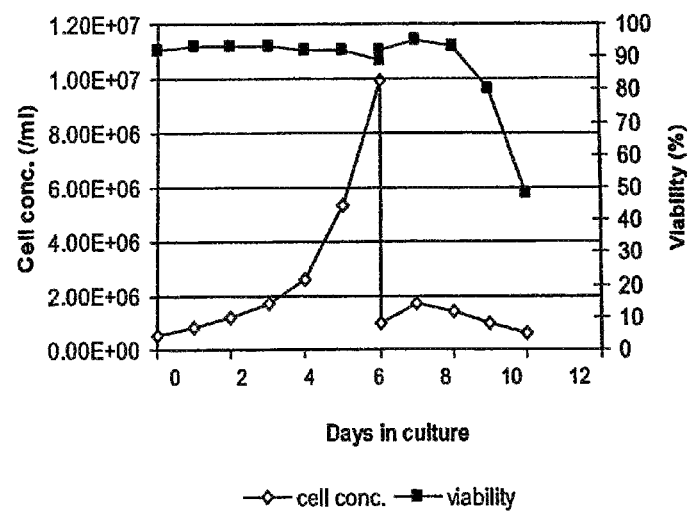
FIG. 4 depicts the cell growth and viability versus days in culture.
Figure 5:
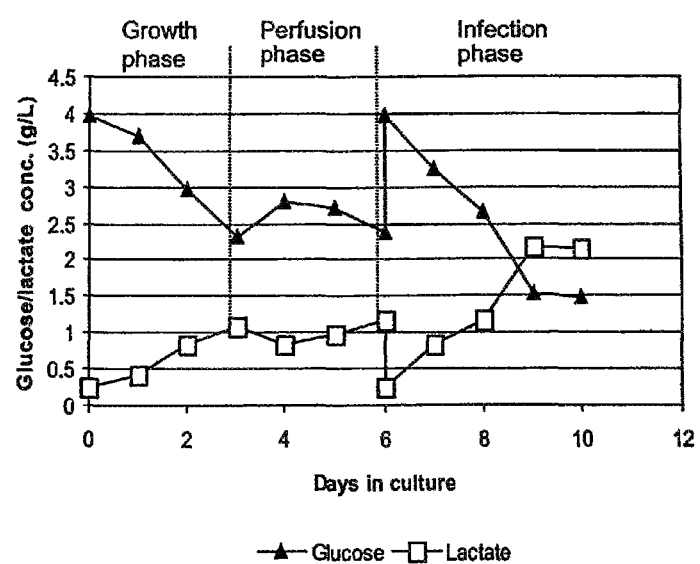
FIG. 5 depicts the glucose and lactate concentrations (g/L) in perfusion culture versus days in culture.

According to this example, cells were cultured and adenoviral vectors produced with medium perfusion using a 10 L (5 L working volume) Wave Bioreactor® 20/50EH (Wave Biotech, LLC) equipped with a YSI-2700 SELECT™ biochemistry analyzer according to the production and purification process depicted in FIG. 1. FIG. 3 depicts a perfusion Wave bioreactor (10) comprising an inflated plastic bag (12) containing cell culture media (14) and an internal flat perfusion filter (16) to provide separation between the cells and spent medium. Media is fed to the bioreactor from a feed bag (18) by feed pump (22) Spent culture medium is withdrawn through the floating filter (16) to a harvest bag (20) by harvest pump (24). Controller (26) controls the functions of the pumps and bioreactor (10). No medium recirculation is required, and consequently this mode of medium perfusion is very gentle to the cells in culture. The wave action minimizes filter clogging during perfusion. The culture volume during perfusion is maintained by a load cell used to trigger fresh medium addition. HEK293 (human epithelial embryonic kidney cells) adapted to serum-free suspension culture according to the method of U.S. Pat. No. 6,194,191 were seeded at $4.8 \times 10^5$ cells/ml and were allowed to grow to $1.2 \times 10^6$ cells/ml in protein-free CD293 medium (Invitrogen™). On day 3 of culture, medium perfusion was started at a cell concentration of $1.7 \times 10^6$ cells/ml. Cell concentration increased approximately exponentially to $1 \times 10^7$ cells/ml on day 6, and cell viability was maintained above 90%. The cell growth the viability and nutrient/metabolite concentrations during culture are shown in FIG. 4 and FIG. 5

The rocking speed was set at 10 and the rocking angle was set at 11. The culture pH was maintained by adjusting CO2 gas percentage delivered by the gas mixer. The dissolved oxygen tension (DOT) in the culture medium was monitored using a disposable DOT probe supplied by Wave Biotech™.

When the cell concentration reached $1 \times 10^7$ cells/ml, the cell culture was diluted 10-fold fold with fresh CD293 medium to supplement nutrients and dilute potentially toxic metabolites into a WAVE BIOTECH™ 200 Bioreactor without a perfusion filter. The cells were then infected with an adenoviral vector (AdCMVp53) at a MOI of 50 vp/cell. AdCMVp53 is a genetically engineered, replication-incompetent human type 5 adenovirus expressing the human wild type p53 protein under control of the cytomegalovirus (CMV) immediate early promoter. Infection was allowed to proceed for 2 days. The culture was harvested on day 2 post-infection. The virus harvest was then subjected to TFF concentration using a PELLICON® 2 mini system fitted with a 500 KD BIOMAX® membrane cassette and subjected to enzyme treatment with BENZONASE®.

Adenoviral vector production was measured using an anion exchange HPLC method. The adenoviral vector concentration in the bioreactor was found to be $1.1 \times 10^{11}$ vp/ml, the virus yield was $1.1 \times 10^{16}$ vp, and the cell-specific vector productivity was 126,000 vp/cell.

Example 2

According to this example, the product of Example 1 was subjected to diafiltration using a tangential flow filtration (TFF) membrane using a PELLICON® 2 mini system fitted with a 500 KD BIOMAX® membrane cassette The clarified harvest was concentrated 20-fold using the PELLICON® 2 mini system prior to diafiltration using a 500 mM Tris buffer at pH 8.0. Diafiltration was performed by the consistent volume method. Fresh diafiltration buffer was continuously added to the system as filtrate was permeated out of the membrane. Studies carried out using the 100 L production scale are set out in Table 5 below. The lack of fetal bovine serum in the culture medium makes is feasible to use TFF membrane partitioning diafiltration as a method of virus purification with high recovery.

TABLE 5

| | Titer (vp/mL) | HPLC Purity (%) | Recovery (%) | Total Yield (vp) |
|---|---|---|---|---|
| Clarified Harvest | $1.2 \times 10^{11}$ | 5.3 | NA | $1.20 \times 10^{16}$ |
| 10-fold DF | $2.3 \times 10^{12}$ | 78.6 | 90 | $1.08 \times 10^{16}$ |
| 20-fold DF | $2.2 \times 10^{12}$ | 89.5 | 89 | $1.07 \times 10^{16}$ |
| 30-Fold DF | $2.3 \times 10^{12}$ | 93.5 | 89 | $1.06 \times 10^{16}$ |
| 40-Fold DF | $1.8 \times 10^{12}$ | 97.1 | 90 | $1.08 \times 10^{16}$ |
| 60-Fold DF | $1.5 \times 10^{12}$ | 98.5 | 79 | $9.50 \times 10^{15}$ |

Table 6 below depicts the infectivity (PFU/vp ratio) of 2 viral vector products produced by the protein free suspension process. Viral particle concentration was determined by $OD_{260}$ analysis and Infections unit (IU) concentration was determined by $TCID_{50}$ assay. This demonstrates that viruses produced by the protein free suspension process are as infectious as those from serum containing production processes.

TABLE 6

| Viral Vectors | Viral particle conc. (vp/mL) | Infections unit conc. (IU/mL) | VP/IU |
|---|---|---|---|
| 1 | $1.2 \times 10^{12}$ | $8 \times 10^{10}$ | 15 |
| 2 | $1.0 \times 10^{12}$ | $6 \times 10^{10}$ | 17 |

Figure 2:
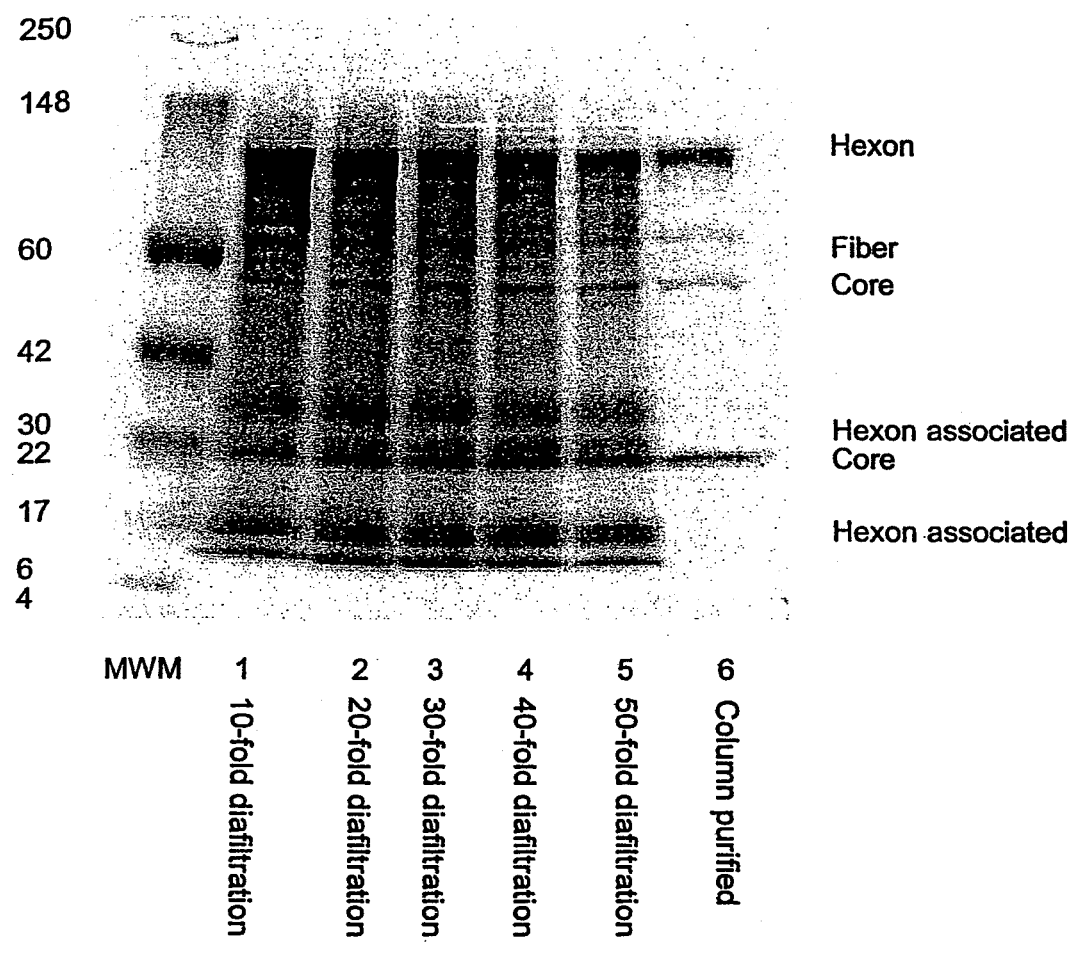
FIG. 2 (Scanned image) depicts analysis of tangential flow filtration (TFF) purified virus, lanes 1-5 and virus purified by conventional methods utilizing a chromatography column.

Each of the resulting diafiltration products described in Table 6 above along with a viral preparation purified by traditional column chromatography were subjected to SDS-PAGE analysis to determine the presence of contaminants. The results depicted in FIG. 2 show that impurities were still present in the diafiltration purified virus preparation even though initial HPCL analysis demonstrated good purity.

The resulting purified viral product was compared to viral preparations prepared by conventional methods utilizing chromatographic purification. SDS-PAGE analysis reveals that the column purified virus is still significantly more pure. While significant purification is realized by the size partitioning as supported by HPLC analysis SDS-PAGE analysis reveals that impurities remain.

Figure 6:
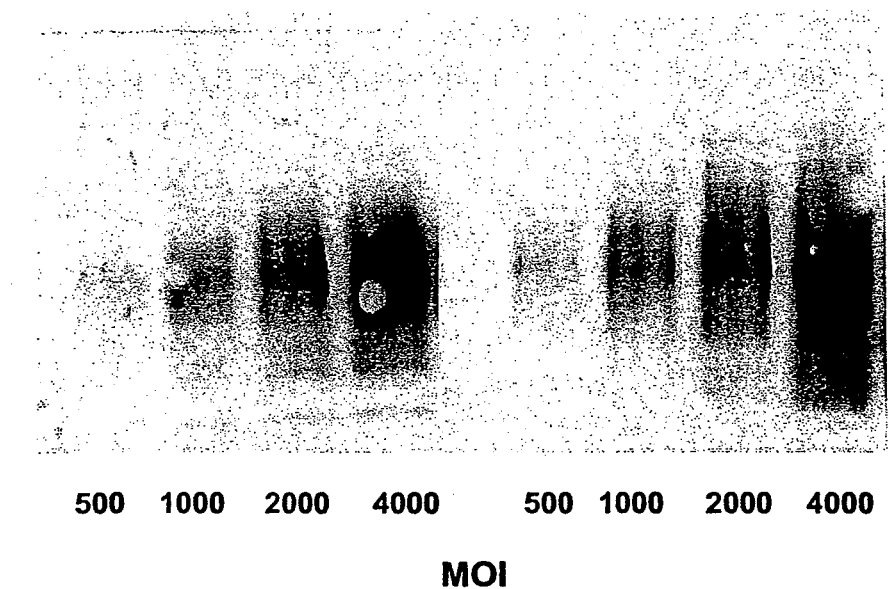
FIG. 6 depicts a comparison of gene expression of viral products produced by CellCube and Wave bioreactor processes.

Further tests were conducted comparing the gene expression of products produced by the Wave bioreactor process with those produced by using CELLCUBE™ bioreactors and are shown in FIG. 6. The virus produced by practice of the Wave suspension process is comparable to that produced by the CELLCUBE™ process in terms of infectiousness and activity.

The use of the wave bioreactor with a suspension culture in a serum-free medium combined with use of tangential flow filtration provides improved scalability and virus yields in the production of purified virus preparations.

All of the methods and compositions disclosed and claimed herein can be made and executed without undue experimentation in light of the present disclosure. While the compositions and methods of this invention have been described in terms of preferred embodiments, it will be apparent to those of skill in the art that variations may be applied to the methods and compositions and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 4,352,883
U.S. Pat. No. 5,670,488
U.S. Pat. No. 5,932,210
U.S. Pat. No. 5,824,544
U.S. Patent Ser. No. 60/026,667
U.S. Patent Ser. No. 60/203,078
Aboud et al., Arch. Virol., 71:185-195, 1982.
Batra et al., Am. 0.1 Respir. Cell Mol Biol., 21(2):238-45, 1999.
Berg, Biotechniques, 14(6):972-978, 1993.
Blackwell et al., Arch. Otolaryngol. Head. Neck Surg., 125(8):856-863, 1999.
Brett et al., J. Immunol., 150:2869-2884, 1993.
Chillon et al., I. Virol., 73(3):2537-40, 1999.
Chroboczek et al., Virology, 186:280-285, 1992.
Cristiano et al., Cancer Detect. Prev., 22(5):445-454, 1998.
Crooks et al., J. Chromatogr., 502(1):59-68, 1990.
Dorai et al., Int. J. Cancer, 82(6):846-52, 1999.
Feldman et al., Cardiovasc. Res., 32(2):194-207, 1996.
Gamier et al., Cytotechnology, 15(1-3):145-155, 1994.
Golasten et al, New Engl J. Med., 309(11983):288-296, 1983.
Graham and Prevec, In: Methods in Molecular Biology: Gene Transfer and Expression Protocol, Murray (Ed.), Humana Press, Clifton, N.J., 7:109-128, 1991.
Graham and Prevec, Mol. Biotechnol., 3(3):207-220, 1995.
Graham et al., J. Gen. Virl, 36(1):59-74, 1977.
Graham, J. Gen. ViroL, 68(Pt 3):937-940, 1987.
Griffiths, J. Histochem. Cytochem., 34(11):1389-1398, 1986.
Han et al., BioL Phann. Bull., 22(8):836-40, 1999.
Hermens and Verhaagen, Prog.-Neurobiol., 55(4):399-432, 1998.
Hollstein et al., Science, 253(5015):49-53, 1991.
Huyghe et al., Human Gene Therapy, 6:1403-1416, 1996.
Hurwitz et al., Hum. Gene Ther., 10:441-48, 1999.
Irie et al., Antisense Nucleic Acid Drug Dev., 9(4):341-9, 1999.
Ishibashi et al, J. Clin. Invest., 92:883-893, 1993.
Ishibashi et al, J. Clin. Invest., 93:1885-1893, 1994.
Jardon and Gamier, Biotechnol Frog., 19(1):202-208, 2003.
Jiang et al., Proc. Nat'l Acad. Sci. USA, 93:9160-9165, 1996.
Jones and Shenk, Cell, 13:181-188, 1978.
Lesch, Biol. Psychiatry, 45(3):247-53, 1999.
Marienfeld et al., Gene Ther., 6(6):1101-13, 1999.
McGrath et al., J. Virol., 25:923-927, 1978.
Mincheff et al., Eur. Urol., 38(2):208-17, 2000.
Mizrahi, Dev. Biol. Stand., 55:219-230, 1983.
Morris et al., Environ. Mol. Mutagen., 27(1):10-8, 1996.
Morrison et al., J. Gen. Virol., 78(Pt 4):873-8, 1997.
O'Neil and Balkovic, Biotechnology, 11(2):173-178, 1993.
Parks et al., J. Virol., 71(4):3293-8, 1997.
PCT Appl. WO 94/17178
PCT Appl. WO 98/00524
Perrin, Vaccine, 13(13):1244-1250, 1995.
Petrof, Eur. Respir. J., 11(2):492-7, 1998.

Phillips et al., In: *Large Scale Mammalian Cell Culture* (Feder and Tolbert, eds.), Academic Press, FL, 1985.
Reddy et al., *Virology,* 251(2):414-26, 1998.
Robbins and Ghivizzani, *Pharmacol Ther,* 80(1):35-47, 1998.
Robbins et al., *Trends Biotechnol.,* 16(1):35-40, 1998.
Smith and Lee, *Anal Biochem.,* 86(1):252-263, 1978.
Stewart et al., *Gene Ther.,* 6(3):350-63, 1999.
Su et al., *Cancer Res.,* 58, 2339-2342, 1998.
Tanzawa et al, *FEBS Letters,* 118(1):81-84, 1980.
van Wezel, *Nature,* 216:64-65, 1967.
Vanderkwaak and Alvarez, *Curr. Opin. Obstet. Gynecol.,* 11(1):29-34, 1999.
Wagner et al., *Science,* 260:1510-1513, 1993.
Wang et al., In: *Animal Cell Technology: Basic and Applied Aspects,* Kaminogawa et al., (eds), 5:463-469, Kluwer Academic Publishers, Netherlands, 1993.
Wang et al., *Cytotechnology,* 9:41-49, 1992.
Wang et al., *Proc. Japan. Soc. Animal Cell Tech.,* 1994.
Watanabe, *Atherosclerosis,* 36:261-268, 1986.
Weinberg, *Science,* 254(5035):1138-1146, 1991.
Wilson, *J. Clin. Invest.,* 98(11):2435, 1996.
Wilson, *Nature,* 365:691-692, 1993.
Yotnda et al., *Gene Ther.,* 8:930-37, 2001.
Zheng et al., *J. Gen. Virol.,* 80(Pt 7):1735-42, 1999.

What is claimed is:

1. A method for removing contaminants from a adenovirus-containing composition comprising obtaining an aqueous composition comprising a selected adenovirus and undesirable contaminants and subjecting the aqueous composition to size partitioning purification using a size partitioning membrane having partitioning pores that retain virus and permit the passage of contaminants there through to remove contaminants and thereby provide a purified virus composition, wherein the virus composition is subjected to at least 10-fold diafiltration, and
wherein the aqueous composition is obtained by a method comprising:
growing host cells in a serum-free medium;
providing nutrients to said host cells;
infecting said host cells with the adenovirus; and
lysing said host cells to provide an aqueous composition comprising adenovirus.

2. The method of claim 1, wherein the membrane has a cutoff threshold below 1000 kDa.

3. The method of claim 1, wherein the membrane has a cutoff threshold of between 100 kDa and 1000 kDa.

4. The method of claim 3, wherein the membrane has a cutoff threshold of between 200 kDa and 600 kDa.

5. The method of claim 4, wherein the membrane has a cutoff threshold of between 300 kDa and 500 kDa.

6. The method of claim 1, wherein the membrane is comprised of regenerated cellulose or polyether sulfone.

7. The method of claim 1, wherein size partitioning purification results in a viral concentration factor of at least 10-fold.

8. The method of claim 1, wherein size partitioning purification results in a viral concentration factor of 20-fold to 100-fold.

9. The method of claim 1, wherein the size partitioning purification comprises tangential ultrafiltration.

10. The method of claim 9, wherein the composition is subjected to filtration through more than one membrane.

11. The method of claim 1, wherein the lysis step is carried out by a process that includes hypotonic solution, hypertonic solution, impinging jet, microfluidization, solid shear, detergent, liquid shear, high pressure extrusion, autolysis or sonication.

12. The method of claim 1, wherein said adenovirus comprises an adenoviral vector encoding an exogenous gene construct operably linked to a promoter.

13. The method of claim 1, wherein said aqueous composition is treated with a nuclease.

14. The method of claim 1, wherein the purified virus composition is subjected to chromatography.

15. A method for isolating adenovirus comprising obtaining an aqueous composition comprising subjecting an aqueous composition comprising a selected adenovirus and undesirable contaminants to filtration through a membrane, wherein the membrane has a cutoff threshold below 1000 kDa, wherein the virus composition is subjected to at least 10-fold diafiltration, and wherein contaminants are eliminated from an adenovirus-containing composition and the adenovirus is retained, and wherein the aqueous composition comprising adenovirus and undesirable contaminants is obtained by a method comprising:
growing host cells in a serum-free medium;
providing nutrients to said host cells;
infecting said host cells with the adenovirus; and
lysing said host cells using detergent to provide the aqueous composition.

16. The method of claim 15, wherein the filtration results in a viral concentration factor of at least 10-fold.

17. The method of claim 15, wherein the filtration comprises tangential ultrafiltration.

18. A method for removing contaminants from a adenovirus-containing composition comprising obtaining an aqueous composition comprising a selected adenovirus and undesirable contaminants and subjecting the aqueous composition to size partitioning purification using a size partitioning membrane having partitioning pores that retain virus and permit the passage of contaminants therethrough to remove contaminants and thereby provide a purified virus composition, wherein the virus composition is subjected to at least 10-fold diafiltration, and wherein the aqueous composition is obtained by a method comprising:
growing host cells in a medium;
providing nutrients to said host cells;
infecting said host cells with the adenovirus; and
lysing said host cells to provide an aqueous composition comprising adenovirus, wherein the lysis step is carried out by a process that includes hypotonic solution, hypertonic solution, impinging jet, microfluidization, solid shear, detergent, liquid shear, high pressure extrusion, autolysis or sonication.

19. The method of claim 18, wherein the membrane has a cutoff threshold below 1000 kDa.

20. The method of claim 18, wherein the membrane has a cutoff threshold of between 100 kDa and 1000 kDa.

21. The method of claim 20, wherein the membrane has a cutoff threshold of between 300 kDa and 500 kDa.

22. The method of claim 18, wherein size partitioning purification results in a viral concentration factor of at least 10-fold.

23. The method of claim 18, wherein the size partitioning purification comprises tangential ultrafiltration.

24. The method of claim 18, wherein the lysis step is carried out using detergent.

25. A method for isolating adenovirus comprising obtaining an aqueous composition comprising subjecting an aqueous composition comprising a selected adenovirus and undesirable contaminants to filtration through a membrane, wherein the membrane has a cutoff threshold below 1000 kDa, wherein the virus composition is subjected to at least 10-fold diafiltration, and wherein contaminants are eliminated from an adenovirus-containing composition and the adenovirus is retained, and wherein the aqueous composition comprising adenovirus and undesirable contaminants is obtained by a method comprising:

growing host cells in a medium;
providing nutrients to said host cells;
infecting said host cells with the adenovirus; and
lysing said host cells to provide the aqueous composition, wherein the lysis step is carried out by a process that includes hypotonic solution, hypertonic solution, impinging jet, microfluidization, solid shear, detergent, liquid shear, high pressure extrusion, autolysis or sonication.

26. The method of claim 25, wherein the filtration results in a viral concentration factor of at least 10-fold.

27. The method of claim 25, wherein the filtration comprises tangential ultrafiltration.

28. The method of claim 1, wherein the purified virus composition is not subjected to chromatography.

* * * * *